United States Patent [19]
Barbier et al.

[11] Patent Number: 6,110,892
[45] Date of Patent: Aug. 29, 2000

[54] PARATHYROID HORMONE ANALOGUES FOR THE TREATMENT OF OSTEOPOROSIS

[75] Inventors: Jean-Rene Barbier, Gatineau; Paul Morley; Witold Neugebauer, both of Ottawa; Virginia J. S. Ross, Gloucester; James F. Whitfield, Ottawa; Gordon E. Willick, Orleans, all of Canada

[73] Assignee: National Research Council of Canada, Ottawa, Canada

[21] Appl. No.: 08/904,760

[22] Filed: Aug. 1, 1997

Related U.S. Application Data

[63] Continuation-in-part of application No. 08/691,647, Aug. 2, 1996, Pat. No. 5,955,425, which is a continuation-in-part of application No. 08/262,495, Jun. 20, 1994, Pat. No. 5,556,940.
[60] Provisional application No. 60/040,560, Mar. 14, 1997.
[51] Int. Cl.$^7$ .................. A61K 38/29; C07K 14/635
[52] U.S. Cl. .............. 514/11; 514/12; 530/317; 530/324
[58] Field of Search ................. 530/317, 324, 530/345; 514/11, 12, 21

[56] References Cited

U.S. PATENT DOCUMENTS

| | | | |
|---|---|---|---|
| 4,587,046 | 5/1986 | Goodman et al. | 530/330 |
| 5,149,779 | 9/1992 | Chorev et al. | 530/317 |
| 5,393,869 | 2/1995 | Nakagawa et al. | 530/324 |
| 5,434,246 | 7/1995 | Fukuda et al. | 530/324 |
| 5,556,940 | 9/1996 | Willick et al. | 530/317 |
| 5,582,995 | 12/1996 | Avruch et al. | 435/69.1 |
| 5,589,452 | 12/1996 | Krestenansky et al. | 514/12 |
| 5,670,483 | 9/1997 | Zhang et al. | 514/14 |
| 5,686,563 | 11/1997 | Kari | 530/326 |
| 5,717,062 | 2/1998 | Chorev et al. | 530/317 |
| 5,723,577 | 3/1998 | Dong | 530/324 |
| 5,747,456 | 5/1998 | Chorev et al. | 514/12 |

FOREIGN PATENT DOCUMENTS

| | | |
|---|---|---|
| 2269176 | 2/1994 | United Kingdom . |
| WO 94/07514 | 4/1994 | WIPO . |
| WO 96/40193 | 12/1996 | WIPO . |

OTHER PUBLICATIONS

Barbier et al, Bioactivities and Secondary Structures of Constrained . . . J. Med. Chem. vol. 40, No. 9, pp. 1373–1380. Apr. 25, 1997.

Proceedings of $13_{th}$ American Peptide Symposium Jun. 1993 pp 556–558 Surewicz et al "Structure–function relationships in human parathyroid hormone: The Essential role of amphiphilic α–helix".

Biochemical and Biophysical Research Communications vol. 181, No. 1, 1991 pp 481–485 Sung et al "Internal Ribosome–Binding Site Directs Expression of Parathyroid Hormone Analogue etc.".

J. of Biological Chemistry vol. 266, No. 5 Feb. 15, 1991 pp. 2831–2835 Sung et al "Specific Degenerate Codons . . .".

(List continued on next page.)

*Primary Examiner*—Jeffrey E. Russel
*Attorney, Agent, or Firm*—Nixon & Vanderhye

[57] ABSTRACT

This invention describes analogues of human parathyroid hormone which have increased activities in bone restoration, and increased bioavailabilities. The peptides described are derivatives of hPTH-(1–31) which are cyclized for example, by formation of lactams between either $Glu^{22}$ and $Lys^{26}$ or $Lys^{26}$ and $Asp^{30}$. In addition, the natural $Lys^{27}$ may be substituted by either a Leu or other hydrophobic residues, such as Ile, norleucine, Met, Val, Ala, Trp, or Phe. Typically, these analogues have enhanced abilities to stimulate adenylyl cyclase in rat osteosarcoma cells, and show increased activities in bone restoration, using the ovariectomized rat model. The analogues also show enhanced activities and bioavailabilities, as demonstrated by their hypotensive effects in the rat. An assay which correlates hypotensive activity with osteogenic activity is also described.

13 Claims, 12 Drawing Sheets

OTHER PUBLICATIONS

Biochemical and Biophysical Research Communications vol. 171, No. 3, 1990 pp 1105–1110 Chakravarthy et al "Parathyroid Hormone Fragment [3–34] Stimulates Protein Kinase C (PKC) . . .".

Endocrinology vol. 130, No. 1, pp 53–60 Jouishomme et al "The Protein Kinase–C Activation . . ."(1992).

J. of Bone and Mineral Research vol. 9, No. 8, 1994 pp 1179–1189 Rixon et al "Parathyroid Hormone . . .".

Biochemistry 1992, 31, pp 2056–2063 Neugebauer et al "Structural Elements of Human Parathyroid . . .".

Int. J. Peptide Protein Res. 43 1994 pp 555–562 Neugebauer et al "Structure and protein kinase C . . .".

Calcif Tissue Int (1996) 58:81–87 Whitfield et al "Stimulation of Growth of Femoral Trabecular Bone . . .".

Inst. Biological Sciences Oct. 1996 Barbier et al "Bioactivities and Secondary Structures . . .".

Inst. Biological Sciences Whitfield et al "Cyclization by a Specific Lactam Increases the Ability . . ."(Not dated–in press).

Calcif Tissue Int (1997) 60:302–308 Whitfield et al "The Hypotensive Actions of Osteogenic . . .".

Calcif Tissue Int (1997) 60:26–29 Whitfield et al "Comparison of the Ability of Recombinant Human . . .".

Neugebauer et al Proceedings of the $22^{nd}$ European Peptide Symposiu,m 1992, Switzerland Cyclized Lactam Analogues of a Human Parathyroid Hormone etc.

H₂N-Ser-Val-Ser-Glu-Ile-Gln-Leu-Met-His-Asn-Leu-Gly-Lys-His-Leu-Asn-Ser-Met-Glu-Arg-Val-Glu-Trp-Leu-Arg-Lys-Lys-Leu-Gln-Asp-Val-COOH

Fig. 1

H₂N-Ser-Val-Ser-Glu-Ile-Gln-Leu-Met-His-Asn-Leu-Gly-Lys-His-Leu-Asn-Ser-Met-Glu-Arg-

Val-Glu-Trp-Leu-Arg-Lys-Leu-Leu-Gln-Asp-Val-NH₂

Fig. 2

H₂N-Ser-Val-Ser-Glu-Ile-Gln-Leu-Met-His-Asn-Leu-Gly-Lys-His-Leu-Asn-Ser-Met-Glu-Arg-

Val-Glu-Trp-Leu-Arg-Lys-Leu-Leu-Gln-Asp-Val-NH₂

Fig. 3

H₂N-Ser-Val-Ser-Glu-Ile-Gln-Leu-Met-His-Asn-Leu-Gly-Lys-His-Leu-Asn-Ser-Met-Glu-Arg-Val-Glu-Trp-Leu-Arg-Lys-Leu-Leu-Gln-Asp-Val-NH₂

Fig. 9

H₂N-Ser-Val-Ser-Glu-Ile-Gln-Leu-Met-His-Asn-Leu-Gly-Lys-His-Leu-Asn-Ser-Met-Glu-Arg-Val-Glu-Trp-Leu-Arg-Lys-Lys-Leu-Gln-Asp-Val-NH₂

Fig. 10

H₂N-Ser-Val-Ser-Glu-Ile-Gln-Leu-Met-His-Asn-Leu-Gly-Lys-His-Leu-Asn-Ser-Met-Glu-Arg-Val-Glu-Trp-Leu-Arg-Lys-Leu-Leu-Gln-Asp-NH₂

Fig. 11

H₂N-Ser-Val-Ser-Glu-Ile-Gln-Leu-Met-His-Asn-Leu-Gly-Lys-His-Leu-Asn-Ser-Met-Glu-Arg-Val-Glu-Trp-Leu-Arg-Lys-Leu-Leu-Gln-Asp-Val-OH

Fig. 15

H₂N-Ser-Val-Ser-Glu-Ile-Gln-Leu-Met-His-Asn-Leu-Gly-Lys-His-Leu-Asn-Ser-Met-Glu-Arg-Val-Glu-Trp-Leu-Arg-Lys-Leu-Leu-Gln-Asp-Val-His-Asn-Phe-NH₂

Fig. 16

H₂N-Ser-Val-Ser-Glu-Ile-Gln-Leu-Met-His-Asn-Leu-Gly-Lys-His-Leu-Asn-Ser-Met-Glu-Arg-Val-Glu-Trp-Leu-Arg-Lys-Leu-Leu-Gln-Asp-Val-His-Asn-Phe-OH

Fig. 17

H$_2$N-Ser-Val-Ser-Glu-Ile-Gln-Leu-Met-His-Asn-Leu-Gly-Lys-His-Leu-Asn-Ser-Met-Glu-Arg-Val-

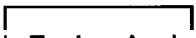
Glu-Trp-Leu-Arg-Lys-Ala-Leu-Gln-Asp-Val-NH$_2$

Fig. 18

H$_2$N-Ser-Val-Ser-Glu-Ile-Gln-Leu-Met-His-Asn-Leu-Gly-Lys-His-Leu-Asn-Ser-Met-Glu-Arg-

Val-Glu-Trp-Leu-Arg-Lys-Nle-Leu-Gln-Asp-Val-NH$_2$

Fig. 19

H$_2$N-Ser-Val-Ser-Glu-Ile-Gln-Leu-Nle-His-Asn-Leu-Gly-Lys-His-Leu-Asn-Ser-Met-Glu-Arg-

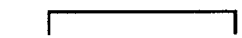
Val-Glu-Trp-Leu-Arg-Lys-Leu-Leu-Gln-Asp-Val-NH$_2$

Fig. 20

H$_2$N-Ser-Val-Ser-Glu-Ile-Gln-Leu-Met-His-Asn-Leu-Gly-Lys-His-Leu-Asn-Ser-Met-Glu-Arg-Val-

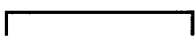
Glu-Trp-Leu-Arg-Lys-Lys-Leu-Gln-Asp-Val-NH$_2$

Fig. 21

H$_2$N-Ser-Val-Ser-Glu-Ile-Gln-Leu-Met-His-Asn-Leu-Gly-Lys-His-Leu-Asn-Ser-Met-Glu-Arg-

Val-Glu-Trp-Leu-Arg-Lys-Ile-Leu-Gln-Asp-Val-NH$_2$

Fig. 22

H$_2$N-Ser-Val-Ser-Glu-Ile-Gln-Leu-Met-His-Asn-Leu-Gly-Lys-His-Leu-Asn-Ser-Met-Glu-Arg-

Val-Glu-Trp-Leu-Arg-Lys-Tyr-Leu-Gln-Asp-Val-NH$_2$

Fig. 23

CH₃COHN-Ser-Val-Ser-Glu-Ile-Gln-Leu-Met-His-Asn-Leu-Gly-Lys-His-Leu-Asn-Ser-Met-Glu-Arg-Val-

Glu-Trp-Leu-Arg-Lys-Leu-Leu-Gln-Asp-Val-NH₂

Fig. 24

H₂N-Ser-Val-Ser-Glu-Ile-Gln-Leu-Met-His-Asn-Leu-Gly-Lys-His-Leu-Asn-Ser-Met-Glu-Arg-

Val-Lys-Trp-Leu-Arg-Glu-Leu-Leu-Gln-Asp-Val-NH₂

Fig. 25

H₂N-Ser-Val-Ser-Glu-Ile-Gln-Leu-Met-His-Asn-Leu-Gly-Lys-His-Leu-Asn-Ser-Met-Glu-Arg-

Val-Asp-Trp-Leu-Arg-Orn-Leu-Leu-Gln-Asp-Val-NH₂

Fig. 26

H₂N-Ser-Val-Ser-Glu-Ile-Gln-Leu-Met-His-Asn-Leu-Gly-Lys-His-Leu-Asn-Ser-Met-Glu-Arg-Val-

Cys-Trp-Leu-Arg-Cys-Leu-Leu-Gln-Asp-Val-NH₂

Fig. 27

H₂N-Ser-Val-Ser-Glu-Ile-Gln-Leu-Met-His-Asn-Leu-Gly-Lys-His-Leu-Asn-Ser-Met-Glu-Arg-

Val-Glu-Trp-Leu-Arg-Cys-Leu-Leu-Gln-Cys-Val-NH₂

Fig. 28

SEQUENCE LISTING (1) GENERAL INFORMATION:

(iii) NUMBER OF SEQUENCES: 35

(2) INFORMATION FOR SEQ ID NO:1:

(i) SEQUENCE CHARACTERISTICS:
      (A) LENGTH: 31 amino acids
      (B) TYPE: amino acid
      (C) STRANDEDNESS:
      (D) TOPOLOGY: linear (ii) MOLECULE TYPE: protein (xi) SEQUENCE DESCRIPTION: SEQ ID NO:1:

```
Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val
            20                  25                  30
```

(2) INFORMATION FOR SEQ ID NO:2:

(i) SEQUENCE CHARACTERISTICS:
      (A) LENGTH: 31 amino acids
      (B) TYPE: amino acid
      (C) STRANDEDNESS:
      (D) TOPOLOGY: linear (ii) MOLECULE TYPE: protein (xi) SEQUENCE DESCRIPTION: SEQ ID NO:2:

Ser Val Ser Glu Ile Gln Leu Met His Asn Leu Gly Lys His Leu Asn
1               5                  10                  15

Ser Met Glu Arg Val Glu Trp Leu Arg Lys Leu Leu Gln Asp Val
            20                  25                  30

(2) INFORMATION FOR SEQ ID NO:3:

(i) SEQUENCE CHARACTERISTICS:
           (A) LENGTH: 31 amino acids
           (B) TYPE: amino acid
           (C) STRANDEDNESS:
           (D) TOPOLOGY: circular (ii) MOLECULE TYPE: protein (ix) FEATURE:
           (D) OTHER INFORMATION: cyclo Glu22-Lys26, and this sequence
               has an amino group c-terminus (NH2).

(xi) SEQUENCE DESCRIPTION: SEQ ID NO:3:

Ser Val Ser Glu Ile Gln Leu Met His Asn Leu Gly Lys His Leu Asn
1               5                  10                  15

Ser Met Glu Arg Val Glu Trp Leu Arg Lys Leu Leu Gln Asp Val
            20                  25                  30

(2) INFORMATION FOR SEQ ID NO:4:

(i) SEQUENCE CHARACTERISTICS:
           (A) LENGTH: 31 amino acids
           (B) TYPE: amino acid
           (C) STRANDEDNESS:
           (D) TOPOLOGY: circular (ii) MOLECULE TYPE: protein (ix) FEATURE:
           (D) OTHER INFORMATION: cyclo Lys26-Asp30, and this sequence
               has an amino group c-terminus (NH2).

(xi) SEQUENCE DESCRIPTION: SEQ ID NO:4:

Ser Val Ser Glu Ile Gln Leu Met His Asn Leu Gly Lys His Leu Asn
1               5                  10                  15

Ser Met Glu Arg Val Glu Trp Leu Arg Lys Leu Leu Gln Asp Val
            20                  25                  30

(2) INFORMATION FOR SEQ ID NO:5:

(i) SEQUENCE CHARACTERISTICS:
           (A) LENGTH: 31 amino acids
           (B) TYPE: amino acid
           (C) STRANDEDNESS:
           (D) TOPOLOGY: linear (ii) MOLECULE TYPE: protein (ix) FEATURE:
           (D) OTHER INFORMATION: This sequence has an amino group
               c-terminus (NH2).

(xi) SEQUENCE DESCRIPTION: SEQ ID NO:5:

Ser Val Ser Glu Ile Gln Leu Met His Asn Leu Gly Lys His Leu Asn
1               5                  10                  15

Ser Met Glu Arg Val Glu Trp Leu Arg Lys Leu Leu Gln Asp Val
            20                  25                  30

(2) INFORMATION FOR SEQ ID NO:6:

(i) SEQUENCE CHARACTERISTICS:
        (A) LENGTH: 31 amino acids
        (B) TYPE: amino acid
        (C) STRANDEDNESS:
        (D) TOPOLOGY: circular (ii) MOLECULE TYPE: protein (ix) FEATURE:
        (D) OTHER INFORMATION: cyclo Lys27-Asp30, and this sequence
            has an amino group c-terminus (NH2).

(xi) SEQUENCE DESCRIPTION: SEQ ID NO:6:

```
Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val
            20                  25                  30
```

(2) INFORMATION FOR SEQ ID NO:7:

(i) SEQUENCE CHARACTERISTICS:
        (A) LENGTH: 30 amino acids
        (B) TYPE: amino acid
        (C) STRANDEDNESS:
        (D) TOPOLOGY: circular (ii) MOLECULE TYPE: protein (ix) FEATURE:
        (D) OTHER INFORMATION: cyclo Glu22-Lys26, and this sequence
            has an amino group c-terminus (NH2).

(xi) SEQUENCE DESCRIPTION: SEQ ID NO:7:

```
Ser Val Ser Glu Ile Gln Leu Met His Asn Leu Gly Lys His Leu Asn
1               5                   10                  15

Ser Met Glu Arg Val Glu Trp Leu Arg Lys Leu Leu Gln Asp
            20                  25                  30
```

(2) INFORMATION FOR SEQ ID NO:8:

(i) SEQUENCE CHARACTERISTICS:
        (A) LENGTH: 31 amino acids
        (B) TYPE: amino acid
        (C) STRANDEDNESS:
        (D) TOPOLOGY: circular (ii) MOLECULE TYPE: protein (ix) FEATURE:
        (D) OTHER INFORMATION: cyclo Glu22-Lys26.

(xi) SEQUENCE DESCRIPTION: SEQ ID NO:8:

```
Ser Val Ser Glu Ile Gln Leu Met His Asn Leu Gly Lys His Leu Asn
1               5                   10                  15

Ser Met Glu Arg Val Glu Trp Leu Arg Lys Leu Leu Gln Asp Val
            20                  25                  30
```

(2) INFORMATION FOR SEQ ID NO:9:

(i) SEQUENCE CHARACTERISTICS:
        (A) LENGTH: 34 amino acids
        (B) TYPE: amino acid
        (C) STRANDEDNESS:
        (D) TOPOLOGY: circular (ii) MOLECULE TYPE: protein (ix) FEATURE:
    (D) OTHER INFORMATION: cyclo Glu22-Lys26, and this sequence
        has an amino group c-terminus (NH2).

(xi) SEQUENCE DESCRIPTION: SEQ ID NO:9:

Ser Val Ser Glu Ile Gln Leu Met His Asn Leu Gly Lys His Leu Asn
1               5                   10                  15

Ser Met Glu Arg Val Glu Trp Leu Arg Lys Ala Leu Gln Asp Val His
            20                  25                  30

Asn Phe (2) INFORMATION FOR SEQ ID NO:10:

(i) SEQUENCE CHARACTERISTICS:
        (A) LENGTH: 34 amino acids
        (B) TYPE: amino acid
        (C) STRANDEDNESS:
        (D) TOPOLOGY: circular (ii) MOLECULE TYPE: protein (ix) FEATURE:
        (D) OTHER INFORMATION: cyclo Glu22-Lys26.

(xi) SEQUENCE DESCRIPTION: SEQ ID NO:10:

Ser Val Ser Glu Ile Gln Leu Met His Asn Leu Gly Lys His Leu Asn
1               5                   10                  15

Ser Met Glu Arg Val Glu Trp Leu Arg Lys Leu Leu Gln Asp Val His
            20                  25                  30

Asn Phe (2) INFORMATION FOR SEQ ID NO:11:

(i) SEQUENCE CHARACTERISTICS:
        (A) LENGTH: 31 amino acids
        (B) TYPE: amino acid
        (C) STRANDEDNESS:
        (D) TOPOLOGY: circular (ii) MOLECULE TYPE: protein (ix) FEATURE:
        (D) OTHER INFORMATION: cyclo Glu22-Lys26, and this sequence
            has an amino group c-terminus (NH2).

(xi) SEQUENCE DESCRIPTION: SEQ ID NO:11:

Ser Val Ser Glu Ile Gln Leu Met His Asn Leu Gly Lys His Leu Asn
1               5                   10                  15

Ser Met Glu Arg Val Glu Trp Leu Arg Lys Ala Leu Gln Asp Val
            20                  25                  30

(2) INFORMATION FOR SEQ ID NO:12:

(i) SEQUENCE CHARACTERISTICS:
        (A) LENGTH: 31 amino acids
        (B) TYPE: amino acid
        (C) STRANDEDNESS:
        (D) TOPOLOGY: circular (ii) MOLECULE TYPE: protein (ix) FEATURE:
        (D) OTHER INFORMATION: cyclo Glu22-Lys26, and this sequence
            has an amino group c-terminus (NH2).

(xi) SEQUENCE DESCRIPTION: SEQ ID NO:12:

```
Ser Val Ser Glu Ile Gln Leu Met His Asn Leu Gly Lys His Leu Asn
1               5                   10                  15

Ser Met Glu Arg Val Glu Trp Leu Arg Lys Xaa Leu Gln Asp Val
            20                  25                  30
```

(2) INFORMATION FOR SEQ ID NO:13:

(i) SEQUENCE CHARACTERISTICS:
        (A) LENGTH: 31 amino acids
        (B) TYPE: amino acid
        (C) STRANDEDNESS:
        (D) TOPOLOGY: circular (ii) MOLECULE TYPE: protein (ix) FEATURE:
        (D) OTHER INFORMATION: cyclo Glu22-Lys26, and this sequence
            has an amino group c-terminus (NH2).

(xi) SEQUENCE DESCRIPTION: SEQ ID NO:13:

```
Ser Val Ser Glu Ile Gln Leu Xaa His Asn Leu Gly Lys His Leu Asn
1               5                   10                  15

Ser Xaa Glu Arg Val Glu Trp Leu Arg Lys Leu Leu Gln Asp Val
            20                  25                  30
```

(2) INFORMATION FOR SEQ ID NO:14:

(i) SEQUENCE CHARACTERISTICS:
        (A) LENGTH: 31 amino acids
        (B) TYPE: amino acid
        (C) STRANDEDNESS:
        (D) TOPOLOGY: circular (ii) MOLECULE TYPE: protein (ix) FEATURE:
        (D) OTHER INFORMATION: cyclo Glu22-Lys26, and this sequence
            has an amino group c-terminus (NH2).

(xi) SEQUENCE DESCRIPTION: SEQ ID NO:14:

```
Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val
            20                  25                  30
```

(2) INFORMATION FOR SEQ ID NO:15:

(i) SEQUENCE CHARACTERISTICS:
        (A) LENGTH: 31 amino acids
        (B) TYPE: amino acid
        (C) STRANDEDNESS:
        (D) TOPOLOGY: circular (ii) MOLECULE TYPE: protein (ix) FEATURE:
        (D) OTHER INFORMATION: cyclo Glu22-Lys26, and this sequence
            has an amino group c-terminus (NH2).

(xi) SEQUENCE DESCRIPTION: SEQ ID NO:15:

```
Ser Val Ser Glu Ile Gln Leu Met His Asn Leu Gly Lys His Leu Asn
1               5                   10                  15

Ser Met Glu Arg Val Glu Trp Leu Arg Lys Ile Leu Gln Asp Val
            20                  25                  30
```

(2) INFORMATION FOR SEQ ID NO:16:

(i) SEQUENCE CHARACTERISTICS:

(A) LENGTH: 31 amino acids
            (B) TYPE: amino acid
            (C) STRANDEDNESS:
            (D) TOPOLOGY: circular (ii) MOLECULE TYPE: protein (ix) FEATURE:
            (D) OTHER INFORMATION: cyclo Glu22-Lys26, and this sequence
                has an amino group c-terminus (NH2).

(xi) SEQUENCE DESCRIPTION: SEQ ID NO:16:

Ser Val Ser Glu Ile Gln Leu Met His Asn Leu Gly Lys His Leu Asn
1               5                  10                  15

Ser Met Glu Arg Val Glu Trp Leu Arg Lys Tyr Leu Gln Asp Val
            20                  25                  30

(2) INFORMATION FOR SEQ ID NO:17:

(i) SEQUENCE CHARACTERISTICS:
            (A) LENGTH: 31 amino acids
            (B) TYPE: amino acid
            (C) STRANDEDNESS:
            (D) TOPOLOGY: circular (ii) MOLECULE TYPE: protein (ix) FEATURE:
            (D) OTHER INFORMATION: cyclo Glu22-Lys26, and this sequence
                has an amino group c-terminus (NH2).

(xi) SEQUENCE DESCRIPTION: SEQ ID NO:17:

Ser Val Ser Glu Ile Gln Leu Met His Asn Leu Gly Lys His Leu Asn
1               5                  10                  15

Ser Met Glu Arg Val Glu Trp Leu Arg Lys Leu Leu Gln Asp Val
            20                  25                  30

(2) INFORMATION FOR SEQ ID NO:18:

(i) SEQUENCE CHARACTERISTICS:
            (A) LENGTH: 31 amino acids
            (B) TYPE: amino acid
            (C) STRANDEDNESS:
            (D) TOPOLOGY: circular (ii) MOLECULE TYPE: protein (ix) FEATURE:
            (D) OTHER INFORMATION: cyclo Lys22-Glu26, and this sequence
                has an amino group c-terminus (NH2).

(xi) SEQUENCE DESCRIPTION: SEQ ID NO:18:

Ser Val Ser Glu Ile Gln Leu Met His Asn Leu Gly Lys His Leu Asn
1               5                  10                  15

Ser Met Glu Arg Val Lys Trp Leu Arg Glu Leu Leu Gln Asp Val
            20                  25                  30

(2) INFORMATION FOR SEQ ID NO:19:

(i) SEQUENCE CHARACTERISTICS:
            (A) LENGTH: 31 amino acids
            (B) TYPE: amino acid
            (C) STRANDEDNESS:
            (D) TOPOLOGY: circular (ii) MOLECULE TYPE: protein (ix) FEATURE:
            (D) OTHER INFORMATION: cyclo Asp22-Orn26, and this sequence
                has an amino group c-terminus (NH2).

(xi) SEQUENCE DESCRIPTION: SEQ ID NO:19:

Ser Val Ser Glu Ile Gln Leu Met His Asn Leu Gly Lys His Leu Asn
1               5                   10                  15

Ser Met Glu Arg Val Asp Trp Leu Arg Xaa Leu Leu Gln Asp Val
            20                  25                  30

(2) INFORMATION FOR SEQ ID NO:20:

(i) SEQUENCE CHARACTERISTICS:
        (A) LENGTH: 31 amino acids
        (B) TYPE: amino acid
        (C) STRANDEDNESS:
        (D) TOPOLOGY: circular (ii) MOLECULE TYPE: protein (ix) FEATURE:
        (D) OTHER INFORMATION: cyclo Cys22-Cys26, and this sequence
            has an amino group c-terminus (NH2).

(xi) SEQUENCE DESCRIPTION: SEQ ID NO:20:

Ser Val Ser Glu Ile Gln Leu Met His Asn Leu Gly Lys His Leu Asn
1               5                   10                  15

Ser Met Glu Arg Val Cys Trp Leu Arg Cys Leu Leu Gln Asp Val
            20                  25                  30

(2) INFORMATION FOR SEQ ID NO:21:

(i) SEQUENCE CHARACTERISTICS:
        (A) LENGTH: 31 amino acids
        (B) TYPE: amino acid
        (C) STRANDEDNESS:
        (D) TOPOLOGY: linear (ii) MOLECULE TYPE: protein (ix) FEATURE:
        (D) OTHER INFORMATION: cyclo Cys26-Cys30, and this sequence
            has an amino group c-terminus (NH2).

(xi) SEQUENCE DESCRIPTION: SEQ ID NO:21:

Ser Val Ser Glu Ile Gln Leu Met His Asn Leu Gly Lys His Leu Asn
1               5                   10                  15

Ser Met Glu Arg Val Glu Trp Leu Arg Cys Leu Leu Gln Cys Val
            20                  25                  30

(2) INFORMATION FOR SEQ ID NO:22:

(i) SEQUENCE CHARACTERISTICS:
        (A) LENGTH: 34 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:22:

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe (2) INFORMATION FOR SEQ ID NO:23:

```
       (i) SEQUENCE CHARACTERISTICS:
           (A) LENGTH: 31 amino acids
           (B) TYPE: amino acid
           (C) STRANDEDNESS:
           (D) TOPOLOGY: linear (ii) MOLECULE TYPE: protein (ix) FEATURE:
           (A) NAME/KEY: Modified-site
           (B) LOCATION: 31
           (D) OTHER INFORMATION: position 31 may be Val, Val-His,
               Val-His-Asn, Val-His-Asn-Phe, Val-His-Asn-Phe-Val,
               Val-His-Asn-Phe-Val-Ala and Val-His-Asn-Phe-Val-Ala-Leu.

(xi) SEQUENCE DESCRIPTION: SEQ ID NO:23:

Xaa Val Ser Glu Ile Gln Leu Xaa His Asn Leu Gly Lys Xaa Xaa Xaa
1               5                   10                  15

Xaa Xaa Glu Arg Val Xaa Trp Leu Xaa Xaa Xaa Leu Xaa Asp Xaa
            20                  25                  30

(2) INFORMATION FOR SEQ ID NO:24:

(i) SEQUENCE CHARACTERISTICS:
           (A) LENGTH: 4 amino acids
           (B) TYPE: amino acid
           (C) STRANDEDNESS:
           (D) TOPOLOGY: linear (ii) MOLECULE TYPE: peptide (xi) SEQUENCE DESCRIPTION: SEQ ID NO:24:

Val His Asn Phe
1

(2) INFORMATION FOR SEQ ID NO:25:

(i) SEQUENCE CHARACTERISTICS:
           (A) LENGTH: 5 amino acids
           (B) TYPE: amino acid
           (C) STRANDEDNESS:
           (D) TOPOLOGY: linear (ii) MOLECULE TYPE: peptide (xi) SEQUENCE DESCRIPTION: SEQ ID NO:25:

Val His Asn Phe Val
1               5

(2) INFORMATION FOR SEQ ID NO:26:

(i) SEQUENCE CHARACTERISTICS:
           (A) LENGTH: 6 amino acids
           (B) TYPE: amino acid
           (C) STRANDEDNESS:
           (D) TOPOLOGY: linear (ii) MOLECULE TYPE: peptide (xi) SEQUENCE DESCRIPTION: SEQ ID NO:26:

Val His Asn Phe Val Ala
1               5

(2) INFORMATION FOR SEQ ID NO:27:

(i) SEQUENCE CHARACTERISTICS:
           (A) LENGTH: 7 amino acids
           (B) TYPE: amino acid
           (C) STRANDEDNESS:
           (D) TOPOLOGY: linear
```

```
      (ii) MOLECULE TYPE: peptide (xi) SEQUENCE DESCRIPTION: SEQ ID NO:27:

Val His Asn Phe Val Ala Leu
1               5

(2) INFORMATION FOR SEQ ID NO:28:

(i) SEQUENCE CHARACTERISTICS:
          (A) LENGTH: 4 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:28:

His Lys Lys Lys
1

(2) INFORMATION FOR SEQ ID NO:29:

(i) SEQUENCE CHARACTERISTICS:
          (A) LENGTH: 4 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:29:

His Leu Lys Lys
1

(2) INFORMATION FOR SEQ ID NO:30:

(i) SEQUENCE CHARACTERISTICS:
          (A) LENGTH: 4 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:30:

Lys Lys Lys Lys
1

(2) INFORMATION FOR SEQ ID NO:31:

(i) SEQUENCE CHARACTERISTICS:
          (A) LENGTH: 4 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:31:

His Leu Lys Ser
1

(2) INFORMATION FOR SEQ ID NO:32:

(i) SEQUENCE CHARACTERISTICS:
          (A) LENGTH: 31 amino acids
          (B) TYPE: amino acid
          (C) STRANDEDNESS:
```

(D) TOPOLOGY: linear (ii) MOLECULE TYPE: protein (ix) FEATURE:
        (D) OTHER INFORMATION: This sequence has an amino group
            c-terminus (NH2).

(xi) SEQUENCE DESCRIPTION: SEQ ID NO:32:

Ser Val Ser Glu Ile Gln Leu Met His Asn Leu Gly Lys His Leu Asn
1               5                  10                  15

Ser Met Glu Arg Val Glu Trp Leu Arg Lys Lys Leu Gln Asp Val
            20                  25                  30

(2) INFORMATION FOR SEQ ID NO:33:

(i) SEQUENCE CHARACTERISTICS:
        (A) LENGTH: 30 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:33:

Ser Val Ser Glu Ile Gln Leu Met His Asn Leu Gly Lys Xaa Xaa Xaa
1               5                  10                  15

Xaa Met Glu Arg Val Xaa Trp Leu Arg Xaa Xaa Leu Gln Xaa
            20                  25                  30

(2) INFORMATION FOR SEQ ID NO:34:

(i) SEQUENCE CHARACTERISTICS:
        (A) LENGTH: 30 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:34:

Ser Val Ser Glu Ile Gln Leu Met His Asn Leu Gly Lys Xaa Xaa Xaa
1               5                  10                  15

Xaa Met Glu Arg Val Xaa Trp Leu Arg Xaa Xaa Leu Gln Xaa
            20                  25                  30

(2) INFORMATION FOR SEQ ID NO:35:

(i) SEQUENCE CHARACTERISTICS:
        (A) LENGTH: 30 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:35:

Ser Val Ser Glu Ile Gln Leu Met His Asn Leu Gly Lys Xaa Xaa Xaa
1               5                  10                  15

Xaa Met Glu Arg Val Xaa Trp Leu Xaa Xaa Xaa Leu Xaa Xaa
            20                  25                  30

PARATHYROID HORMONE ANALOGUES FOR THE TREATMENT OF OSTEOPOROSIS

CROSS-REFERENCE TO RELATED APPLICATIONS

This application is a Continuation-in-Part of U.S. application Ser. No. 08/691,647, filed Aug. 2, 1996, now U.S. Pat. No. 5,955,425, which is a continuation-in-part of application Ser. No. 08/262,495, filed Jun. 20, 1994, now U.S. Pat. No. 5,556,940 and this application also claims benefit of U.S. provisional Application No. 60/040,560, filed Mar. 14, 1997.

FIELD OF THE INVENTION

This invention relates to analogues of human parathyroid hormone, which have been found to be effective in the treatment of osteoporosis.

BACKGROUND OF THE INVENTION

Osteoporosis is a leading cause of disability in the elderly, particularly elderly women. It has recently been realized that human parathyroid hormone (hPTH) and certain analogues are stimulators of bone growth that are useful in the treatment of osteoporosis. Osteoporosis is a progressive disease which results in the reduction of total bone mass and increased bone fragility. This often results in spontaneous fractures of load-bearing bones and the physical and mental deterioration characteristic of immobilizing injuries. Post-menopausal osteoporosis is caused by the disappearance of estrogens which trigger a decade-long acceleration of bone turnover with an increased imbalance between resorption of old bone and formation of new bone. This results in thinning, increased porosity, and trabecular depletion of load-bearing bones. Osteoporosis is also associated with hyperthyroidism, hyperparathyroidism, Cushing's syndrome, and the use of certain steroidal drugs. Remedies historically have involved increase in dietary calcium, estrogen therapy, and increased doses of vitamin D, but mainly with agents such as antiresorptives that inhibit bone resorption by osteoclasts.

Parathyroid hormone (PTH) is produced by the parathyroid gland and is a major regulator of blood calcium levels. PTH is a polypeptide and synthetic polypeptides may be prepared by the method disclosed by Erickson and Merrifield, *The Proteins,* Neurath et al, Eds., Academic Press, New York, 1976, page 257, and as modified by the method of Hodges et al (1988), *Peptide Research* 1, 19, or by Atherton, E. and Sheppard, R. C., *Solid Phase Peptide Synthesis, IRL Press, Oxford,* 1989.

When serum calcium is reduced to below a normal level, the parathyroid gland releases PTH and the calcium level is increased by resorption of bone calcium, by increased absorption of calcium from the intestine, and by increased renal reabsorption of calcium from nascent urine in the kidney tubules. Although continuously infused low levels of PTH can remove calcium from the bone, the same low doses, when intermittently injected can actually promote bone growth.

Tregear, U.S. Pat. No. 4,086,196, described human PTH analogues and claimed that the first 27 to 34 amino acids are the most effective in terms of the stimulation of adenylyl cyclase in an in vitro cell assay. Rosenblatt, U.S. Pat. No. 4,771,124, disclosed the property of hPTH analogues wherein $Trp^{23}$ is substituted by amino acids phenylalanine, leucine, norleucine, valine, tyrosine, β-naphthylalanine, or α-naphthylalanine as a PTH antagonist. These modified hPTH analogues also have the 2 and 6 amino terminal acids removed, resulting in loss of most agonist activities when used to treat osteoporosis. These analogues were designed as inhibitors or PTH and PTH-related peptide. The analogues were claimed as possibly useful in the treatment of hypercalcemia associated with some tumors.

Pang et al, WO93/06845, published Apr. 15, 1993, described analogues of hPTH which involve substitutions of $Arg^{25}$, $Lys^{26}$, $Lys^{27}$ with numerous amino acids, including alanine, asparagine, aspartic acid, cysteine, glutamine, glutamic acid, glycine, histidine, isoleucine, leucine, methionine, phenylalanine, proline, serine, threonine, tryptophan, tyrosine, or valine. These are claimed, with no supporting data from animal or human trials, to be effective in the treatment of osteoporosis with minimal effects on blood pressure and smooth muscle.

PTH operates through activation of two second messenger systems, $G_s$-protein activated adenylyl cyclase (AC) and $G_q$-protein activated phospholipase $C_\beta$. The latter results in a stimulation of membrane-bound protein kinase Cs (PKC) activity. The PKC activity has been shown to require PTH residues 29 to 32 (Jouishomme et al (1994) *J. Bone Mineral Res.* 9, (1179–1189). It has been established that the increase in bone growth, i.e. that effect which is useful in the treatment of osteoporosis, is coupled to the ability of the peptide sequence to increase AC activity. The native PTH sequence has been shown to have all of these activities. The hPTH-(1–34) sequence is typically shown as (A):

```
Ser Val Ser Glu Ile Gln Leu Met His Asn Leu Gly Lys His Leu
    Asn Ser Met Glu Arg Val Glu Trp Leu Arg Lys Lys Leu Gln
    Asp Val His Asn Phe-OH (SEQ ID NO:22)         A
```

The following linear analogue, hPTH-(1–31)-$NH_2$, for which data is included in Table 1, below, has only AC-stimulating activity and has been shown to be fully active in the restoration of bone loss in the ovariectomized rat model (Rixon, R. H. et al (1994) *J. Bone Miner. Res.* 9, 1179–1189; Whitfield et al (1996), *Calcified Tissue Int.* 58, 81–87; Willick et al, U.S. Pat. No. 5,556,940 issued Sep. 17, 1996):

```
Ser Val Ser Glu Ile Gln Leu Met His Asn Leu Gly Lys His Leu
    Asn Ser Met Glu Arg Val Glu Trp Leu Arg Lys Lys Leu Gln
    Asp Val-NH2                                    B
```

The above molecule, B SEQ ID NO:32, and its counterpart with a $Leu^{27}$ substitution SEQ ID NO:2 may have a free carboxyl ending instead of the amide ending illustrated.

It is an object of the present invention to produce new PTH analogues with greater metabolic stability, increased bone restoration activity, increased AC activity, and minimal clinical side effects.

BRIEF SUMMARY OF THE INVENTION

According to one aspect of the invention, human parathyroid hormone hPTH and pharmaceutically acceptable salts thereof are provided, having the amino acid sequence R-NH-R1-Val-Ser-Glu-Ile-Gln-Leu-R2-His-Asn-Leu-Gly-Lys-R3-R4-R5-R6-R7-Glu-Arg-Val-R8-Trp-Leu-R9-R10-R11-Leu-R12-Asp-Y (SEQ ID NO:23)

wherein,
R=hydrogen or any linear or branched chain alkyl, acyl or aryl group,
R1=Ser, Ala or Aib,
R2=Met, or a naturally occurring hydrophobic amino acid, R3=His or a water soluble amino acid, R4=Leu or a water soluble amino acid, R5=Asn or a water soluble amino acid, R6=Ser or a water soluble amino acid, R7=Met, or a naturally occurring hydrophobic amino acid, R8=Glu, Lys or Asp, R9=Arg, Cys, Lys, Orn, or His R10=Arg, Lys, Orn, Gln, Glu or Asp R11=a naturally occurring hydrophobic or polar amino acid, R12=Gln, Arg, Glu, Asp, Lys or Orn, Cterm=OH, $NH_2$, and Y=Cterm, Val-Cterm, Val-His-Cterm, Val-His-Asn-Cterm, Val-His-Asn-Phe-Cterm, Val-His-Asn-Phe-Val-Cterm, Val-His-Asn-Phe, Val-Ala-Cterm and Val-His-Asn-Phe, Val-Ala-Leu-Cterm, (SEQ ID NOS:24–27) cyclized as between one or two amino acid pairs 22 and 26, 26 and 30, 27 and 30, and 25 and 29 are lactams when R9 is Lys or Orn and R12 is Glu or Asp, excluding cyclo($Lys^{26}$-$Asp^{30}$)[$Leu^{27}$]-hPTH-(1–34)-$NH_2$, cyclo($Lys^{27}$-$Asp^{30}$)-h-PTH-(1–34)-$NH_2$ and cyclo($Lys^{26}$-$Asp^{30}$)-[$Leu^{27}$]-hPTH-(1–34)-OH.

Examples of the salts include salts of inorganic acids, salts of organic acids such as formic acid, acetic acid, tartaric acid and citric acid, salts of inorganic bases such as sodium and ammonium and salts of organic bases such as triethylamine, ethylamine and methylamine.

According to another feature of the present invention, cyclisation is effected by the formation of lactams, involving the coupling of the side-chains of the selected amino acid pairs such as between natural residues 22 and 26, or 26 and 30. Other types of cyclisations, such as the formation of a disulfide bridge e.g., between Cys containing analogues $Cys^{22}$-$Cys^{26}$ and $Cys^{26}$-$Cys^{30}$ are also contemplated.

Preferred aspects of the invention include human parathyroid hormone hPTH analogues or pharmaceutically acceptable salts thereof having the amino acid sequence: H-NH-Ser-Val-Ser-Glu-Ile-Gln-Leu-Met-His-Asn-Leu-Gly-Lys-R3-R4-R5-R6-Met-Glu-Arg-Val-R8-Trp-Leu-Arg-R10-R11-Leu-Gln-R13-$NH_2$ (SEQ ID NO:33) where R3=His or a water soluble amino acid, R4=Leu or a water soluble amino acid, R5-Asn or a water soluble amino acid, R6=Ser or a water soluble amino acid, R8=Glu or Cys, R10=Cys, R11=Lys or Leu, R13=Asp or Cys, cyclized in the form of a disulfide bridge between Cys pairs 22/26 or 26/30.

Also disclosed are human parathyroid hormone hPTH analogues or pharmaceutically acceptable salts thereof having the amino acid sequence: H-NH-Ser-Val-Ser-Glu-Ile-Gln-Leu-Met-His-Asn-Leu-Gly-Lys-R3-R4-R5-R6-Met-Glu-Arg-Val-R8-Trp-Leu-Arg-R10-R11-Leu-Gln-R13-OH (SEQ ID NO:34) where R3=His or a water soluble amino acid, R4=Leu or a water soluble amino acid, R5=Asn or a water soluble amino acid, R6=Ser or a water soluble amino acid, R8=Glu or Cys, R10=Cys, R11=Lys, Leu, and R13=Asp, or Cys, cyclized in the form of a disulfide bridge between Cys pairs 22/26 or 26/30.

Also disclosed are human parathyroid hormone hPTH analogues or pharmaceutically acceptable salts thereof having the amino acid sequence: H-NH-Ser-Val-Ser-Glu-Ile-Gln-Leu-Met-His-Asn-Leu-Gly-Lys-R3-R4-R5-R6-Met-Glu-Arg-Val-R8-Trp-Leu-R9-R10-R11-Leu-R12-R13-$NH_2$ (SEQ ID NO:35) where R3=His or a water soluble amino acid, R4=Leu or a water soluble amino acid, R5=Asn or a water soluble amino acid, R6=Ser or a water soluble amino acid, R8=Lys, Asp, Cys, Orn or Glu, R9=Arg, Cys, Lys, Orn, His or Glu, R10=Glu, Orn, Cys, Asp or Lys, R11=Lys, Gln, Ile, Nle, Leu, Tyr, Ala or Asp, R12=Gln, Glu, Asp, Lys or Orn and R13=Asp, Cys, Glu, Orn or Lys, cyclized in the form of a lactam between amino acid pairs 22 and 26; 26 and 30; or 27 and 30 when R11 and R13 are Lys or Asp; or 25 and 29 when R9 and R12 are Lys, Orn, Glu or Asp, or cyclized in the form of a disulfide bridge between Cys pairs 22/26, 26/30 or 25/29.

Substitutions of various amino acids have also been found to be effective. $Lys^{27}$ may be replaced by a Leu or by various other naturally occurring hydrophobic or polar residues. Another factor is how well the residue fits to the receptor. Ala is not as hydrophobic as Leu. Lys and Tyr are generally considered to be polar, but nonetheless have hydrophobic interactions with the receptor. Lys, for example, can fold so that the hydrophobic part interacts with other hydrophobic residues in the receptor, and the $NH_2$ is exposed to solvent. Such substitutions include ornithine, citrulline, α-aminobutyric acid, alanine, norleucine, isoleucine and tyrosine, or any linear or branched α-amino aliphatic acid, having 2–10 carbons in the side chain, any such analogue having a polar or charged group at the terminus of the aliphatic chain. Examples of polar or charged groups include: amino, carboxyl, acetamido, guanido and ureido. Although it appears that $Leu^{27}$ is the best substitution, it also appears that many other pos27 substitutions retain nearly full activity and could also have desired properties, such as increased proteolytic stability or water solubility. Ile, norleucine, Met, and ornithine are expected to be the most active.

This substitution results in a stabilization of an α-helix in the receptor-binding region of the hormone. This has been confirmed by examination of the circular dichroism spectrum of the lactam analogues, as compared to the circular dichroism spectrum of the linear molecule, [$Leu^{27}$]-hPTH-1-31)-$NH_2$. Circular dichroism spectra are highly sensitive to the presence of α-helical secondary structure, and the technique has been used to demonstrate the presence of α-helix in hPTH fragments (Neugebauer et al (1991) *Biochemistry* 31, 2056–2063). Furthermore, the stabilization of α-helix on formation of the above-mentioned lactams in hPTH-(20–34)-$NH_2$ has been shown (Neugebauer et al (1994) *Int. J. Protein Peptide Res.* 43, 555–562). There is a potential amphiphilic α-helix between residues 21 and 31 of hPTH-(1–31)-$NH_2$, and data has been presented showing that the hydrophobic face of this helix interacts with the PTH receptor (Neugebauer, W. (1995) et al *Biochemistry* 34, 8835–8842; Gardella, T. J. et al (1993), *Endocrinology* 132, 2024–2030).

It has been found that the most effective cyclisation involves the formation of a lactam, for example, between either residues $Glu^{22}$ and $Lys^{26}$, or $Lys^{26}$ and $Asp^{30}$. Other cyclisations are also possible such as between $Lys^{27}$ and $Asp^{30}$, although this lactam has been found to exhibit some de-stabilizing effect on the α-helix.

More specifically, receptor-binding studies of PTH fragments have indicated a principal binding region within residues 14–34.[1] We have suggested that the residues 17–29 α-helix binds as such to the PTH receptor, and that the amphiphilic portion of this α-helix binds with its hydrophobic face to the receptor.[2] This model is consistent with the results of a study of receptor binding-region analogues.[3]

NMR studies have shown that even a model peptide found to be highly helical by CD also populates many non-helical conformations. Thus, the structure of a receptor-bound peptide hormone, such as PTH, cannot be inferred reliably from its free structure in solution. Constrained analogues of peptide hormones have been used to limit the number of conformational states available to the peptide[8]. Examination of the sequence of hPTH reveals 3 possible salt bridges within residues 17–29 which could either stabilize or destablize α-helix. These are between $Glu^{22}$ and $Lys^{26}$, and $Lys^{26}$ and $Asp^{30}$, both of which are expected to stabilize an α-helix, and between $Lys^{27}$ and $Asp^{30}$, which is expected to destablize an α-helix.[4] Lactam formation between these residue pairs would restrict the conformations available to hPTH in this helical region. Furthermore, two of these lactams, $Glu^{22}$-$Lys^{26}$ and $Lys^{26}$-$Asp^{30}$ which are expected to stabilize α-helical structure are located on the polar face of the amphiphilic portion of the α-helix. The third one, $Lys^{27}$-$Asp^{30}$, is expected to at least partially destabilize α-helix and involves a residue, $Lys^{27}$, which is on the hydrophobic face of the amphiphilic helix. Cyclisation as between positions 25 and 29 can occur if Lys or Orn replaces Arg in position 25, and if $Gln^{29}$ is replaced with Glu or Asp.

The substitution of Leu for the $Lys^{27}$ results in a more hydrophobic residue on the hydrophobic face of the amphiphilic helix. This resulted in increased adenylyl cyclase stimulating activity in the ROS cell time. It will be appreciated by those skilled in the art that other such substitutions discussed above would likely result in analogues with the same or increased activities.

The combined effect of substitution and either lactam formation is expected to stabilize the α-helix and increase bioactivity, and to protect this region of the molecule from proteolytic degradation. The presence of the amide at the C-terminus is preferred in the sense that it is further expected to protect the peptide against exoproteolytic degradation, although some peptidases can hydrolyze them. (Leslie, F. M. and Goldstein, A. (1982) *Neuropeptides* 2, 185–196).

It has also been found that other amino acid substitutions can usefully be made. Specifically, we have replaced the oxidation sensitive Met residue at positions 8, 18 with a naturally occurring hydrophobic residue, Nle, as per Japanese Patent publication 61-24598. It is also to be expected that other such hydrophobic residues like Leu, Ile, Val, Phe and Trp would also be useful, as per U.S. Pat. No. 5,393,869 to Nakagawa et al.

Reverse lactams are also contemplated. For example, we have shown the effectiveness of a $Lys^{22}$-$Glu^{26}$ switch. It is therefore to be expected that similar switches could usefully be made as between the 26–30 and 27–30 lactams.

Another substitution at the preferred 22–26 lactam site, in addition to the aforementioned Cys-Cys, ie $Asp^{22}$-$Orn^{26}$ has been done to illustrate that different cyclisation/ring sizes can usefully be made.

In the U.S. Pat. No. 5,393,869 Nakagawa et al and U.S. Pat. No. 5,434,246, Fukuda et al some substituted hPTH analogues were reported to have substantial AC activity and might have enhanced stabilities to proteolytic attack, specifically.

1. Ser-1 to Aib (α-aminoIsobutyric acid)
2. Lys-27 to Gln (reported to have 2.5×AC activity)
3. Residues 14, 15, 16, 17 to Lys, in whole or in part (reported to greatly increase activity—up to 8×. This may be due to increase in water solubility. In vivo, these are expected to be more labile to trypsin-like enzymes). They claim this tetrapeptide (residues 14–17, incl.) such that there is at least one water soluble amino acid. For example His-14 or Lys-14; Leu-15, Lys-15 or Arg-15; Asn-16, Orn-16, Hci-16, Asp-16, Arg-16, Lys-16, Lys-16, Ser-16 or Gly-16; and Ser-17, Lys-17, Asp-17 or Arg-17. Could also include Glu, for example.
4. Arg 25 to His to minimize protease attack. Since our lactams, particularly with Leu or another hydrophobic amino acid at position-27, can become somewhat insoluble and also difficult to dissolve, it would be expected that the same substitutions would be useful in our lactams.

It will also be appreciated by those skilled in the art that although the 1–31 h-PTH cyclics may be preferred, it is to be expected from the data presented herein that cyclic fragments in the range of 1–30 to 1–37 will also be effective. In particular, there is no evidence in the literature that the presence of additional amino acids up to 37 affect the biological properties of the hormone, particularly given the confirmatory 1–34 data included herein.

The lactams according to the invention may be prepared by known procedures described below, and may be used for stimulating bone growth, for restoring bone, and for the promotion of bone healing in various circumstances, such as in the treatment of osteoporosis and normal fractures.

BRIEF DESCRIPTION OF THE DRAWINGS

FIG. 1 shows the structure of natural human PTH, residues 1–31 (SEQ ID NO:1);

FIG. 2 shows the structure of $[Leu^{27}]cyclo(Glu^{22}$-$Lys^{26})$-hPTH-(1–31)-$NH_2$ (SEQ ID NO:3);

FIG. 3 shows the structure of $[Leu^{27}]cyclo(Lys^{26}$-$Asp^{30})$-hPTH-(1–31)-$NH_2$ (SEQ ID NO:4);

FIG. 9 shows the structure of $[Leu^{27}]$-hPTH-(1–31)-$NH_2$ (SEQ ID NO:5);

FIG. 10 shows the structure of $cyclo(Lys^{27}$-$Asp^{30})$-hPTH-(1–31)-$NH_2$ (SEQ ID NO:6);

FIG. 11 shows the structure of $[Leu^{27}]cyclo(Glu22$-$Lys^{26})$-hPTH-(1–30)-$NH_2$ (SEQ ID NO:7);

FIG. 15 shows the structure of [Leu$^{27}$]cyclo[Glu$^{22}$-Lys$^{26}$)-hPTH-(1–31)-OH (SEQ ID NO:8);

FIG. 16 shows the structure of [Leu$^{27}$]cyclo(Glu$^{22}$-Lys$^{26}$)-hPTH-(1–34)-NH$_2$ (SEQ ID NO:9);

FIG. 17 shows the structure of [Leu$^{27}$]cyclo(Glu$^{22}$-Lys$^{26}$)-hPTH-(1–34)-OH (SEQ ID NO:10);

FIG. 18 shows the structure of [Ala$^{27}$]cyclo(Glu$^{22}$-Lys$^{26}$)-hPTH-(1–31)-NH$_2$ SEQ ID NO:11);

FIG. 19 shows the structure of [Nle$^{27}$]cyclo(Glu$^{22}$-Lys$^{26}$)-hPTH-(1–31)-NH$_2$ (SEQ ID NO:12);

FIG. 20 shows the structure of [Nle$^{8,18}$; Leu$^{27}$]cyclo(Glu$^{22}$-Lys$^{26}$)-hPTH-(1–31)-NH$_2$ (SEQ ID NO:13);

FIG. 21 shows the structure of cyclo(Glu$^{22}$-Lys$^{26}$)-hPTH-(1–31)-NH$_2$ (SEQ ID NO:14);

FIG. 22 shows the structure of [Ile$^{27}$]cyclo(Glu$^{22}$-Lys$^{26}$)-hPTH-(1–31)-NH$_2$ (SEQ ID NO:15);

FIG. 23 shows the structure of [Tyr$^{27}$]cyclo(Glu$^{22}$-Lys$^{26}$)-hPTH-(1–31)-NH$_2$ (SEQ ID NO:16);

FIG. 24 shows the structure of α-acetyl-[Leu$^{27}$]cyclo(Glu$^{22}$-Lys$^{26}$)-hPTH-(1–31)-NH$_2$ (SEQ ID NO:17);

FIG. 25 shows the structure of [Leu$^{27}$]cyclo(Lys$^{22}$-Glu$^{26}$)-hPTH-(1–31)-NH$_2$ (SEQ ID NO:18);

FIG. 26 shows the structure of [Leu$^{27}$]cyclo(Asp$^{22}$Orn$^{26}$)-hPTH-(1–31)-NH$_2$ (SEQ ID NO:19);

FIG. 27 shows the structure of [Cys$^{22}$; Cys$^{26}$; Leu$^{27}$]cyclo(Cys$^{22}$-Cys$^{26}$)-hPTH-(1–31)-NH$_2$ (SEQ ID NO:20), and FIG. 28 shows the structure of [Cys$^{26}$; Cys$^{30}$; Leu$^{27}$]cyclo(Cys$^{26}$-Cys$^{30}$)-hPTH-(1–31)-NH$_2$ (SEQ ID NO:21).

PREPARATION OF HORMONE ANALOGUES

Figure 4:
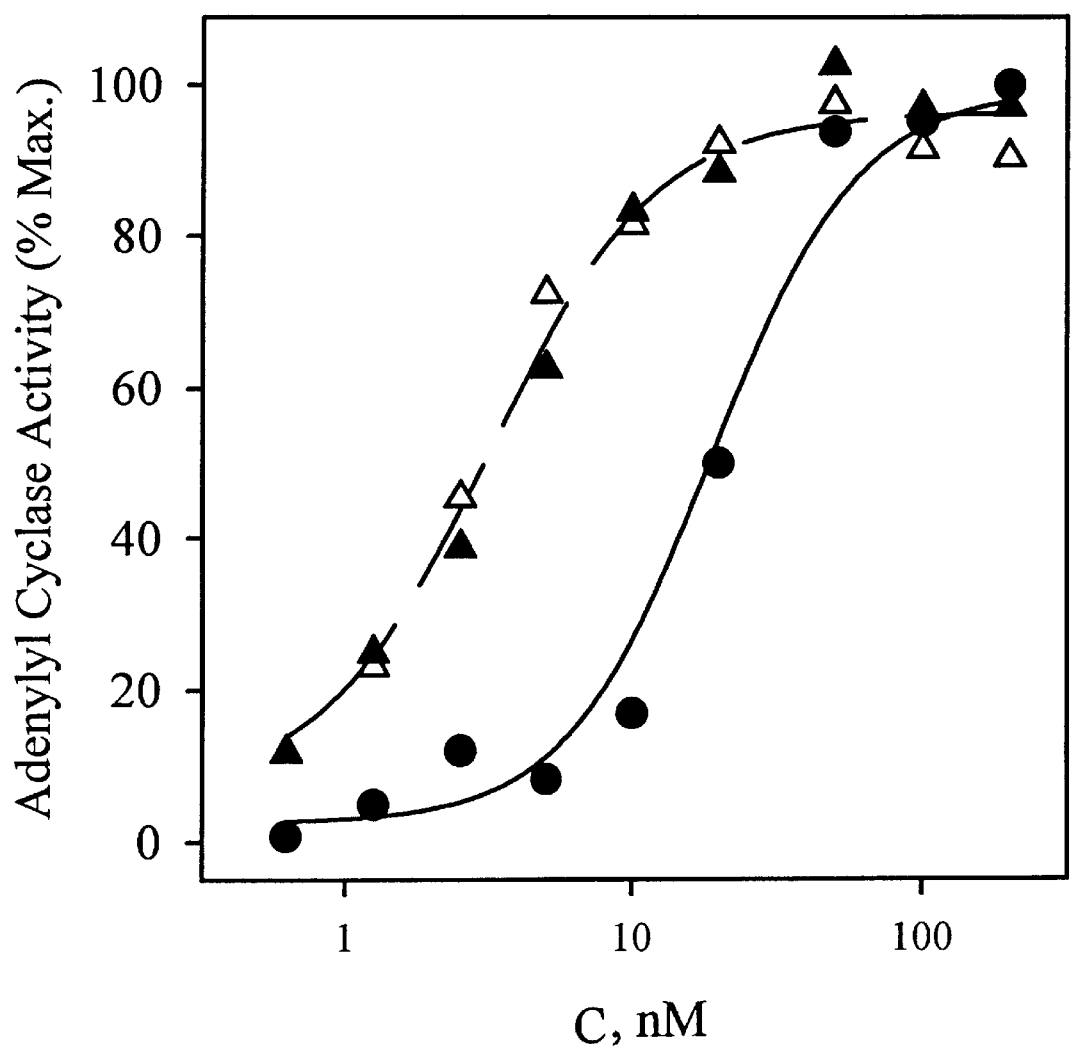
FIG. 4 shows the activities of the analogues according to the invention in adenylyl cyclase stimulation of ROS 17/2 cells.

The technique of solid phase peptide synthesis developed by R. B. Merrifield ("Solid-Phase Peptide Synthesis", Advances in Enzymology 32, 221–296, 1969), incorporated herein by reference, is widely and successfully used for the synthesis of polypeptides such as parathyroid hormone. The strategy is based on having the carboxyl-terminus amino acid of the peptide attached to a solid support. Successive amino acids are then added in high yield. The N-terminal α-amino group is protected in such a way that this protecting group can be removed without removal of the peptide from the solid support. The chemistry used here involves a modification of the original Merrifield method, referred to as the Fmoc approach. The Fmoc (fluorenylmethoxycarbonyl) group can be removed by mild alkaline conditions, which leaves the alkali stable side-chain protecting groups and the link to the support untouched. This technique is described by E. Atherton and R. C. Sheppard, "Solid Phase Peptide Synthesis; a Practical Approach", IRL Press, New York, N.Y., incorporated herein by reference.

EXAMPLE 1

Synthesis and Purification of Linear hPTH-(1–31)-amide Analogues

The α-amino groups of the amino acids were protected by 9-fluorenylmethoxycarbonyl (Fmoc) during coupling. Couplings were performed with a mixture of hydroxybenzotriazole (HOBt), 2-(1H-benzotriazole-1-yl)-1,1,3,3-tetramethyluronium tetrafluoroborate (TBTU), and diisopropylethylamine (DIPEA). A 4-fold excess of activated amino acids was used with double coupling on addition of the Asn, Gln, His, Val, and Ile residues. The coupling times for Arg and Gly additions were increased from 30 to 60 minutes. Coupling of the first residue (Val$^{31}$) to the support (Tentagel® R, Rapp Polymere, Tubingen, Germany) was performed manually. All other steps were performed on a PepSeptive Biosystems® Model 9050 Plus automated peptide synthesizer. Side chain protections were as follows: Arg (2,2,5,7,8-pentamethylchroman-6-sulfonyl); Glu, Asp, and Ser (τ-butyl); His, Gln, and Asn (trityl); Trp (t-butyloxycarbonyl).

After Fmoc removal from the N-terminal Ser, the peptide resin was washed with DCM, then cleaved from the resin by shaking with 7.5 ml of reagent K (6.19 ml TFA 0.38 ml each of water, 90% phenol/water, and thioanisole, and 0.19 ml of 1,2-ethanedithiol) for 4 hr. at 20° C. The cleaved peptide mixture was removed by filtration, and precipitated by addition to τ-butyl-methylether. The precipitate was collected by centrifugation, washed 2× with τ-butyl-methylether, then dried by vacuum centrifugation.

The crude product was dissolved in 14 ml of 15% acetonitrile/water, 0.1% TFA and chromatographed on a Vydac® C$_{18}$-column (10μ, 1×25 cm). The product was eluted with a 1%/min. gradient of acetonitrile (14–40%) in 0.1% TFA in water. The purity of the final product was estimated by analytical HPLC on a Vydac® C$_{18}$ column (10μ, 0.4×25 cm), and by molecular mass assay on an electrospray mass spectrometer (VG Quattro). The data for hPTH-(1–31)-NH$_2$ so formed, is given in Table 1 below.

EXAMPLE 2

Synthesis and Purification of Cyclic Analogues

[Leu$^{27}$]cyclo(Glu$^{22}$-Lys$^{26}$)-hPTH-(1–31)-NH$_2$. This peptide was synthesized as described in Example 1, with Lys-Alloc and Glu-OAll substituted at position 26 and 22, respectively. After the addition of Fmoc-Ser$^{17}$, the peptide-resin was removed from the column to a reaction vial (Minivial®, Applied Science), suspended in 1.7 ml of a solution of tetrakis (triphenylphosphine)palladium(0) (0.24 mmol), 5% acetic acid and 2.5% N-methylmorpholine (NMM) in dichloromethane (DCM) under argon, then shaken at 20° C. for 6 hr to remove the allyl and alloc protecting groups (Solé, N. A. et al (1993) in Peptides: Chemistry, Structure, and Biology, Smith, J. and Hodges, R. (Eds), ESCOM pp. 93–94), incorporated herein by reference. The peptide resin was then washed with 0.5% diethyldithiocarbamate (DEDT), 0.5% NMM in DMF (50 ml), followed by DMF (50 ml) and DCM (50 ml). The peptide (0.06 mmol) was cyclized by shaking with 0.06 mmol of 1-hydroxy-7-azabenzotriazole (HOAt)/0.12 mmol NMM in 2 ml DMF for 14 h at 20° C. (Carpino, L. A. (1993) J. Am. Chem. Soc. 115, 4397–4398). The peptide-resin was filtered, then washed once with DMF, repacked into the column, and washed with DMF until bubbles were removed from the suspension. The remaining synthesis was carried out as with Example 1 except that the N-terminal Fmoc group was not removed. The Fmoc-peptide was cleaved from the resin with reagent K as described above. The HPLC was carried out as in Example 1, with the Fmoc group removed prior to the final HPLC.

Analogue [Leu$^{27}$]cyclo(Lys$^{26}$-Asp$^{30}$)-hPTH-(1–31)-NH$_2$ was prepared in an analogous manner.

EXAMPLE 3

Adenylyl Cyclase Assays

The ability of the hPTH analogues to bind to receptors and activate the adenylyl cyclase coupled signalling mechanism was determined on a differentiation-competent osteoblast-like ROS 17/2 rat osteosarcoma (ROS) cell line. This activity is known to be tightly coupled to the ability of the analogue to restore bone mass in the ovariectomized rat. Adenylyl cyclase-stimulating activity was estimated by prelabelling the cellular ATP pool with [$^3$H]-adenine and then measuring the amount of [$^3$H]-cyclic AMP produced from the [$^3$H]-ATP during the first 10 min of exposure to a particular analogue. This was based on the procedure described by Whitfield et al, *J. Cellular Physiology* 150, 299–303, 1992, incorporated herein by reference.

The adenylyl cyclase results are expressed in Table 2 below as the concentration necessary to express a half-maximal increase in the AC activity. The data is also displayed in FIG. 4. In FIG. 4, the closed circles show the adenylyl cyclase-stimulating activity of hPTH-(1–31)-NH$_2$, and the activities of [Leu$^{27}$]cyclo(Glu$^{22}$-Lys$^{26}$)-hPTH-(1–31)-NH$_2$ and [Leu$^{27}$]cyclo(Lys$^{26}$-Asp$^{30}$)-hPTH-(1–31)-NH$_2$ are shown by open and closed triangles, respectively.

EXAMPLE 4

Figure 14:
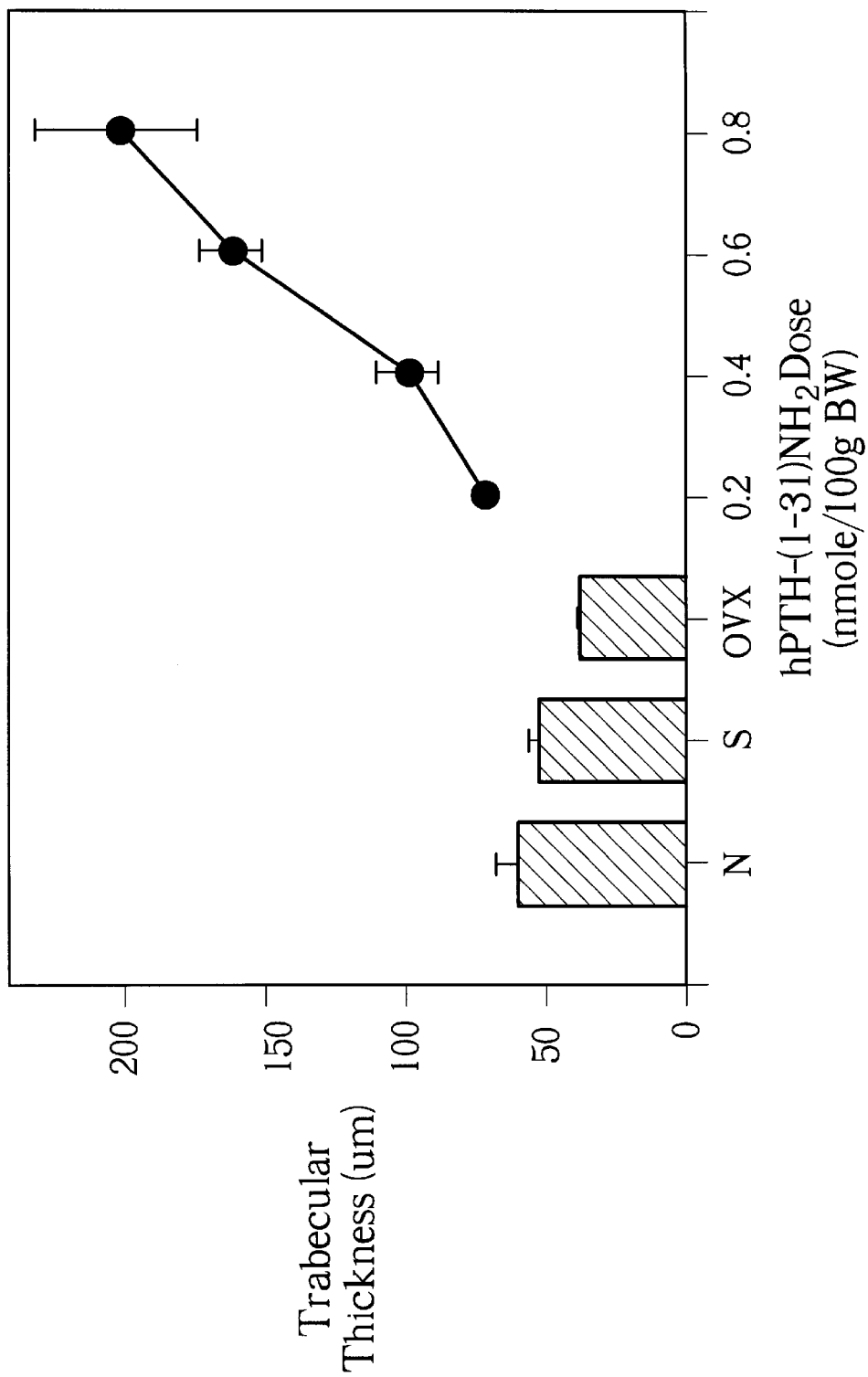
FIG. 14 is a graph illustrating the effect on bone growth of different dosages of linear hPTH-(1–31)-NH$_2$.

Determination of Anabotic Activities of hPTH Analogues With Ovariectomized Rat Model Dosages Doses were based upon dose-response data on hPTH (1–31)-NH$_2$. The bone-building potency of hPTH-(1–31) NH$_2$ was tested using several doses (0.8, 0.6, 0.4, and 0.2 nmole/100 g of body weight) and a regenerative or treatment-assessing, rather than preventative, model.[11] Ovariectomized 3-months-old rats, were left for 9 weeks to let the mostly non-lameliar femoral trabecular bone be severely depleted before starting the 6 weeks of daily injections. By the end of the 9th week they had lost about 75% of their femoral trabecular bone mass. FIG. 14 shows the dose-dependent increase in the mean trabecular thicknesses caused by lameliar deposition that had been produced by the 36 injections of 4 different doses of the fragment. The fragment could also stimulate trabecular bone growth in much older rates. Thus, 36 injections of the mid-range dose of 0.6 nmole/100 g of body weight of hPTH-(1–31)NH$_2$ were able to significantly increase the mean trabecular thickness above the normal starting value in the predepleted (9 weeks after OVX) femoral trabecular bone of 1-year-old rats, and they did so as effectively as hPTH-(1–84). Accordingly, the dosage of 0.6 nmole/100 g of body weight was used in further tests.

A full description of the protocol is given in Rixon et al, *J. Bone & Mineral Research* 9, 1179–1189, 1994 and Whitfield et al *Calcif. Tissue Int.* 58, 81–87, 1996 incorporated herein by reference. Normal, Sham-OVX (ovariectomized), and OVX Sprague-Dawley rats (3 months-old; 255–260 g) were purchased from Charles River Laboratories (St. Constant, QC). The rats were randomized into groups of 8 animals which received Purina rat chow and water ad libitum. There were no unscheduled deaths. The animals received 6, once-daily subcutaneous injections/week starting at the end of the second week after OVX, and ending at the end of the 8th week after OVX (i.e., 36 injections). Eight Sham-OVX and 8 OVX controls rats received 36 injections of vehicle (0.15 M NaCl containing 0.001N HCl) while 8 OVX rats received 0.6 nmole of fragment in vehicle/100 g of body weight). At the end of the 8th week after OVX, femurs were removed isolated, cleaned, and cut in half at mid-diaphysis and the proximal half was discarded. After removing the epiphysis, each half-femur was split lengthwise into two parts and the bone marrow was flushed out.

The bone-building potencies of the fragments were assessed from the changes in the mean thicknesses (area/perimeter) of the trabeculae in the distal half-femurs from the variously treated animals. To measure mean trabecular thickness, the two demineralized half-femurs from each rat were dehydrated and embedded in paraffin. Longitudinal, 10-μm sections from the middle plane of each bone were cut and then strained with Sanderson's rapid bone stain (Surgipath Medical Industries, Inc., Winnipeg, MB, Canada). The mean trabecular thickness was measured using a M4 imaging system and bone morphometric software from Imaging Research Inc., (St. Catherines, ON, Canada).

Figure 5:
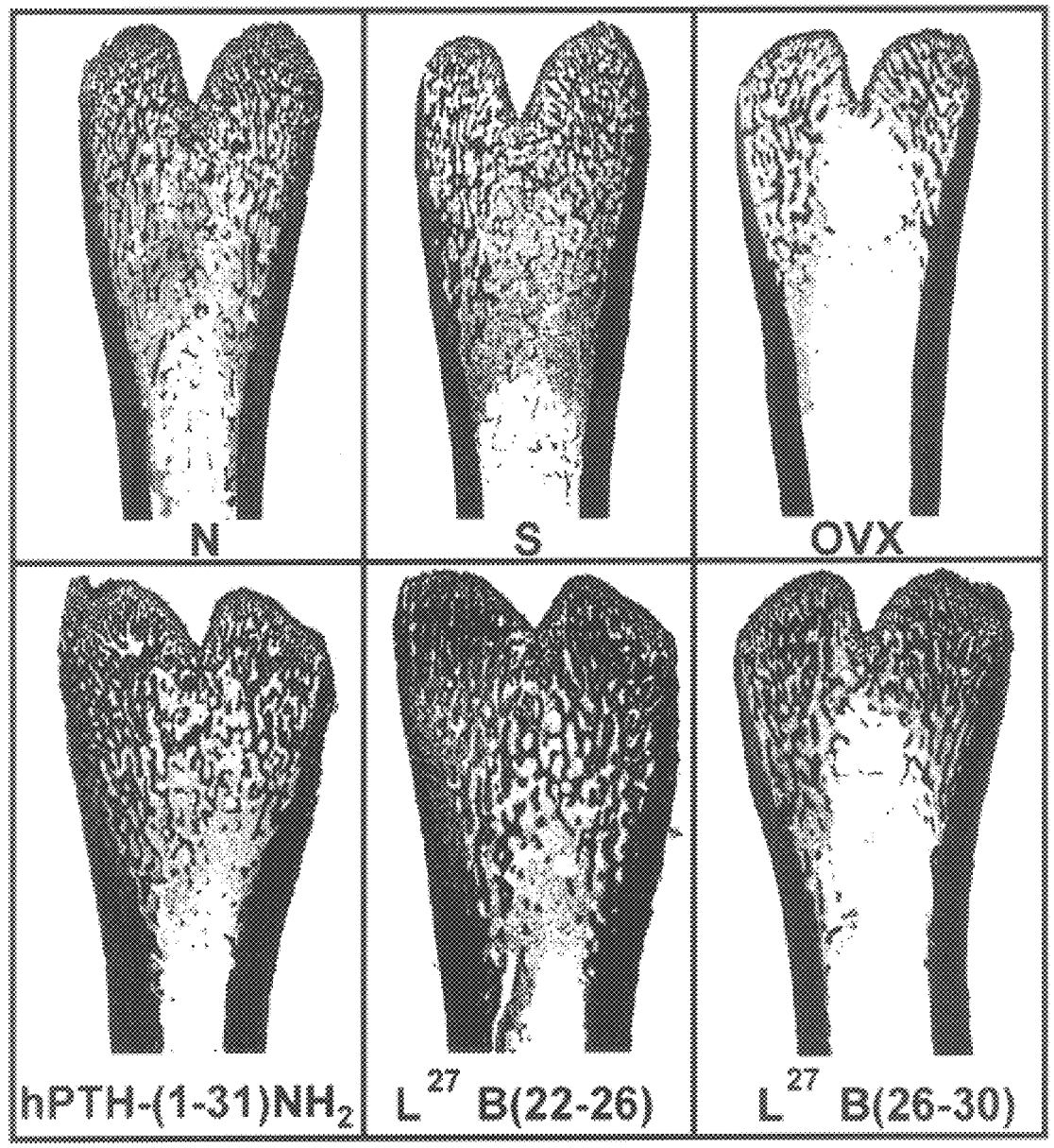
FIG. 5 shows representative histological sections of bones prepared at the end of 8 weeks after OVX, illustrating the different abilities of hPTH-(1–31)$NH_2$ and its lactam derivatives to prevent bone loss and to stimulate bone growth in ovariectomized (OVX) Sprague-Dawley rats.
Figure 7:
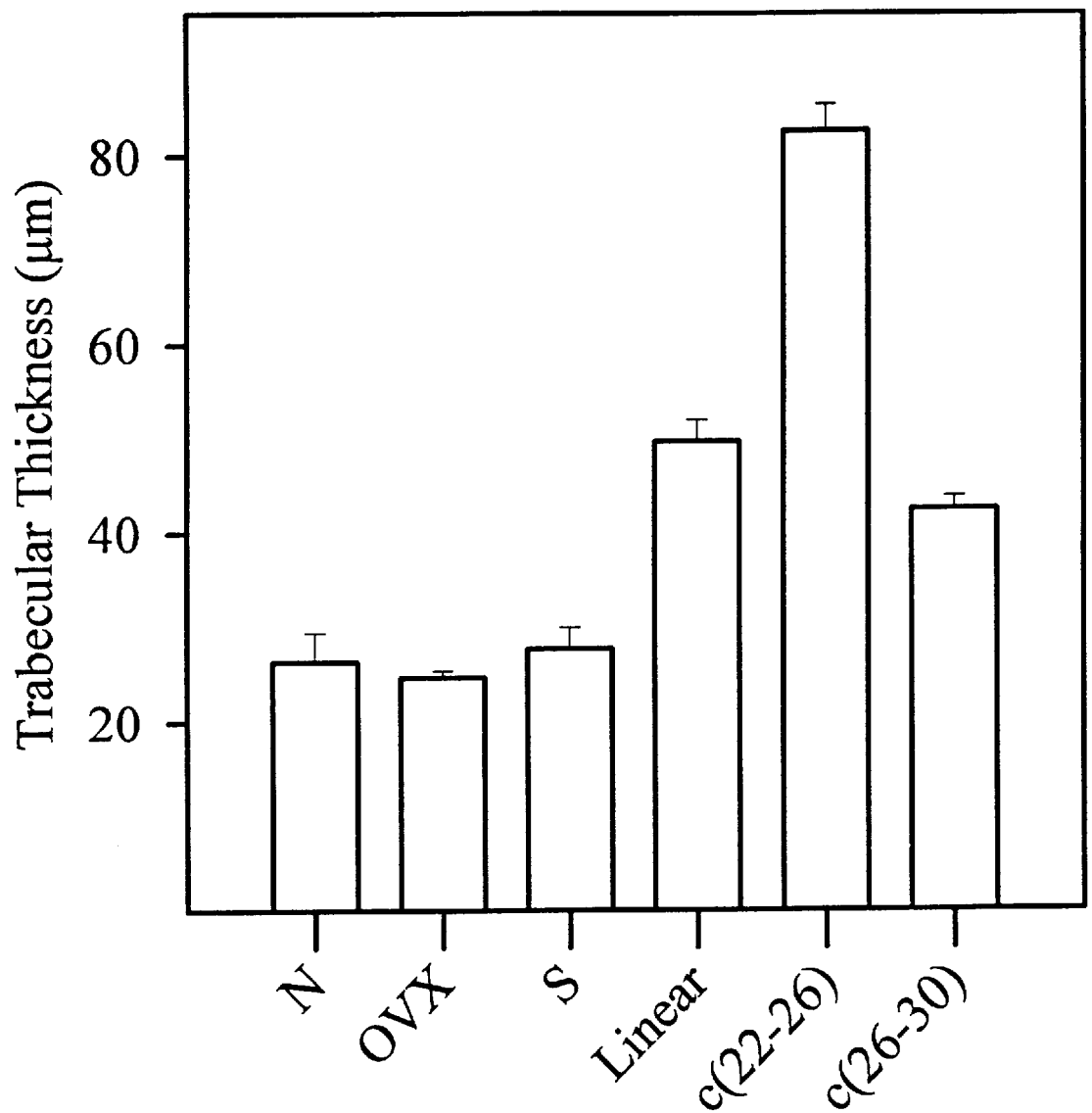
FIG. 7 shows trabecular thicknesses of rat femurs for normal, ovariectomized (OVX), sham and animals treated with hPTH-(1–31)-$NH_2$, $[Leu^{27}]cyclo(Glu^{22}$-$Lys^{26})$-hPTH-(1–31)-$NH_2$, and $[Leu^{27}]cyclo(Lys^{26}$-$Asp^{30})$-hPTH-(1–31)-$NH_2$.

Representative histological sections of bones prepared at the end of 8 weeks after OVX are shown in FIG. 5. The results are further presented in the form of a bar graph in FIG. 7. The bar shows the values for trabecular thickness of the normal, ovariectomized (OVX), sham, hPTH-(1–31)-NH$_2$, [Leu$^{27}$]cyclo(Glu$^2$-Lys$^{26}$)-hPTH-(1–31)-NH$_2$, and [Leu$^{27}$]cyclo(Lys$^{26}$-Asp$^{30}$)-hPTH-(1–31)-NH$_2$. [Leu$^{27}$] cyclo(Glu$^2$-Lys$^{26}$)-hPTH-(1–31)-NH$_2$ shows an especially superior activity compared to the linear analogue, hPTH-(1–31)-NH$_2$. This linear analogue has been shown to be fully active in bone restoration, but uses only one cellular signalling (the AC-activated) pathway. Thus, these cyclic analogues, like their linear analogue, are expected to have fewer undesired clinical side-effects than their longer counterparts, such as hPTH-(1–34) or hPTH-(1–84), which activate both cellular signalling mechanisms.

EXAMPLE 5

Figure 6:
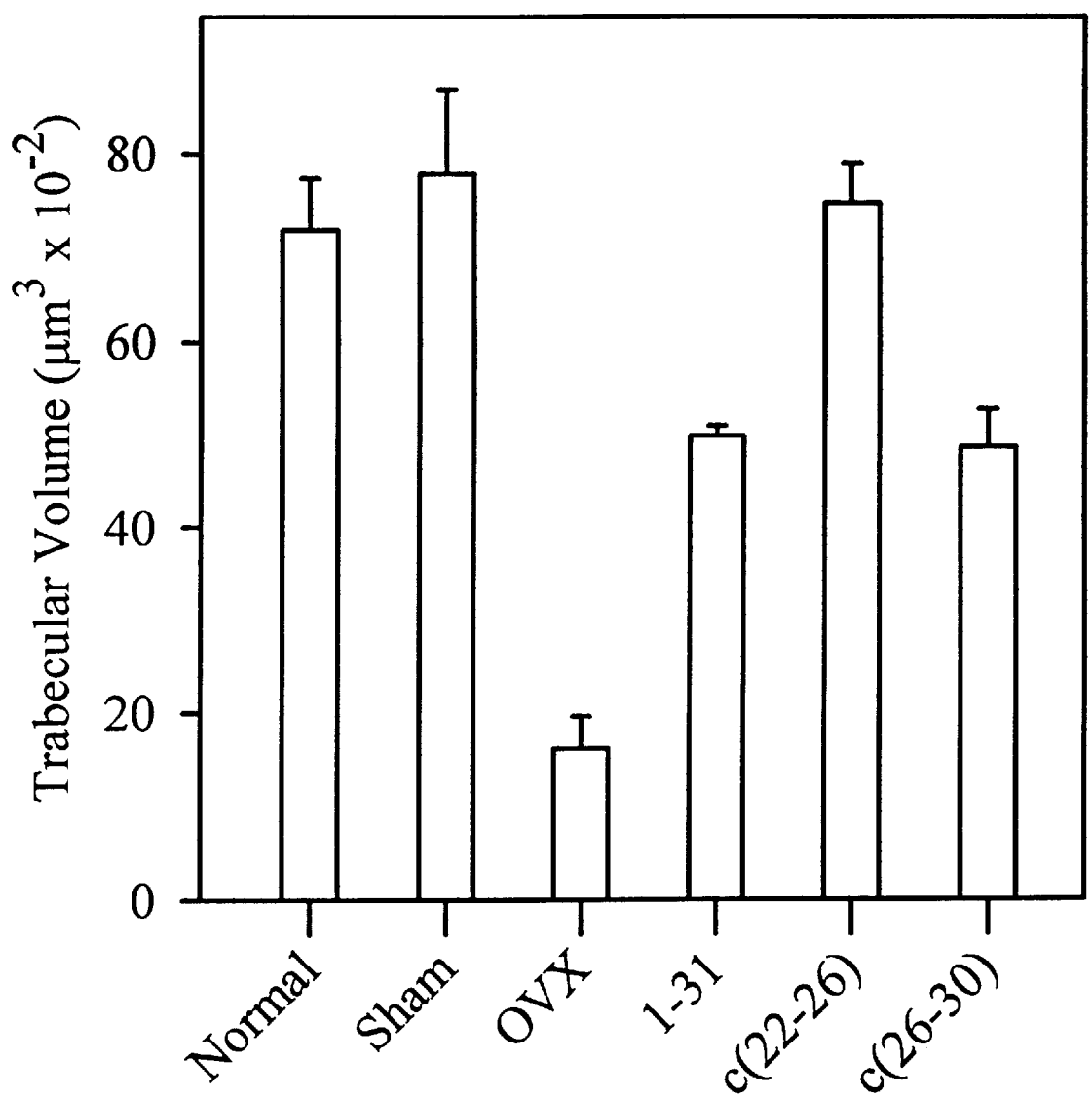
FIG. 6 shows the trabecular bone volume of control animals and hPTH analogue treated animals for rats initially severely depleted of bone. Treatment of the animals began 9 weeks after OVX. $[Leu^{27}]cyclo[Glu^{22}$-$Lys^{26}]$hPTH-(1–31)-$NH_2$ was the most effective of the fragments, restoring the bones to the values in normal control rats.

Bone Restoration by hPTH Analogues of Rats With Severely Depleted Trabecular Bone In this second example of bone restoration, the abilities of the lactam fragments to restore severely depleted trabecular bone are compared. In this experiment, the 6-week program of once-daily injections of 0.6 nmole of peptide/100 g of body weight of young sexually mature rats was delayed until the end of the 9th week after OVX. At this time, 75% of their trabecular bone had been lost. As can be seen in FIG. 6, [Leu$^{27}$]cyclo[Glu$^{22}$-Lys$^{26}$]-hPTH-(1–31)NH$_2$ was the most effective of the fragments. It restored the trabecular bone volume to the values in normal control rats.

EXAMPLE 6

Hypotensive Effects of hPTH Analogues

Figure 8:
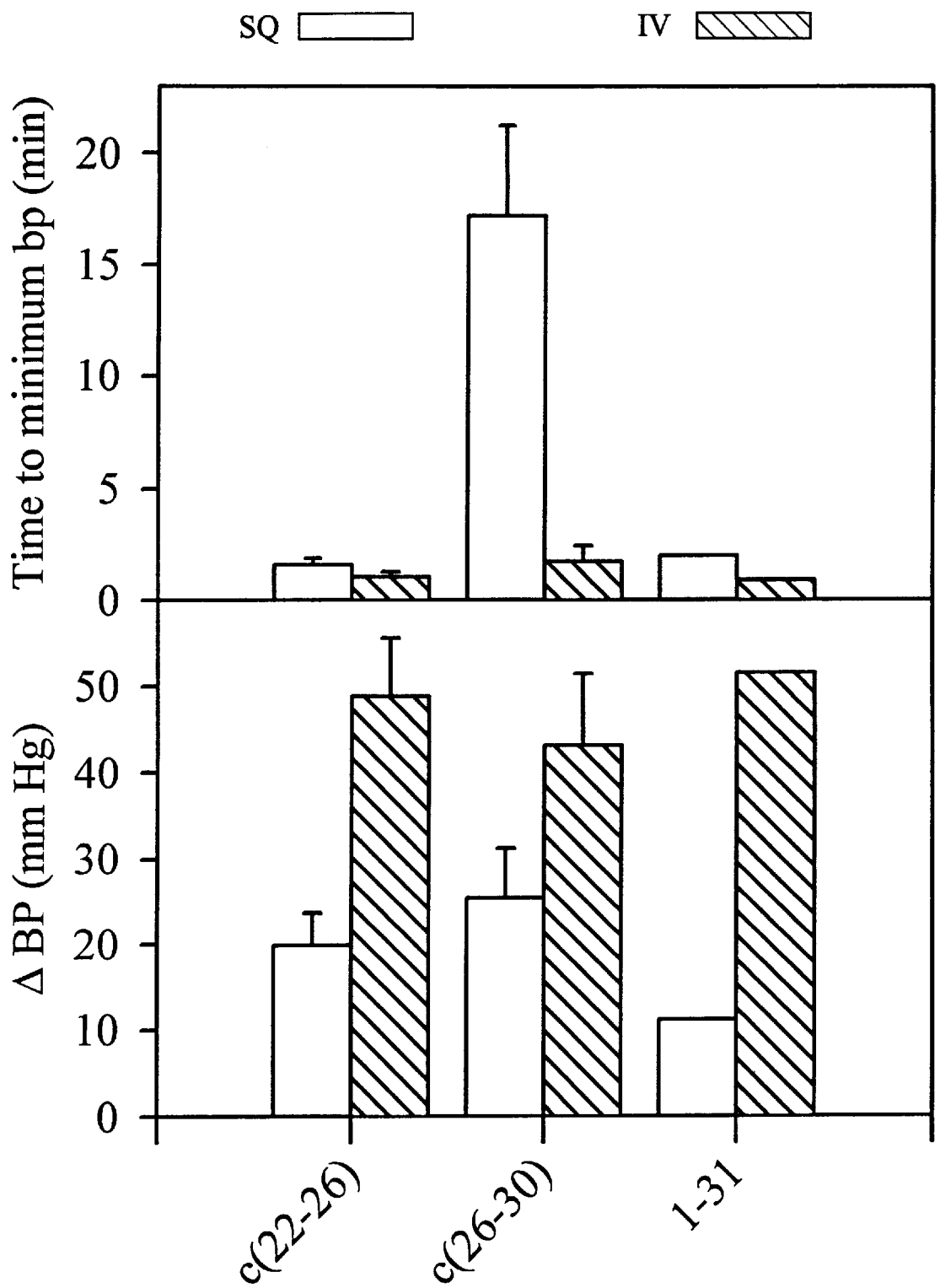
FIG. 8 shows the maximum drop in blood pressure and time to maximum drop in blood pressure on addition of 0.8 nmol/100 g dose of hPTH-(1–31)-$NH_2$, $[Leu^{77}]cyclo(Glu^{22}$-$Lys^{26})$hPTH-(1–31)-$NH_2$ or $[Leu^{27}]cyclo(Lys^{26}$-$Asp^{30})$hPTH-(1–31)-$NH_2$. Peptides were administered either subcutaneously (open bar) or intravenously (hatched bar)

Female Sprague-Dawley rats (weighing over 290 g) were anesthetized with intraperitoneally injected sodium pentobarbital (65 mg/kg body weight). Rectal temperature was monitored with a YS1402 thermistor (Yellow Springs Instrument Co., Inc. Yellow Springs, Ohio) and maintained between 36.0 and 38.5° C. throughout the experiment. Ear pinna temperature was also monitored using a YSi banjo thermistor. The tail artery was exposed to cannulated with a Jelco 25-gIV catheter (Johnson and Johnson Medical Inc., Arlington, Tex.) and connected to a Statham pressure transducer, the signals from which were recorded digitally with a Biopac Systems MP100 Monitor (Harvard Instruments, Saint Laurent, QC, Canada). For intravenous injection of PTH or one of its fragments, a femoral vein was also exposed. After surgery, the rat was allowed to stabilize for 8 min after which PTH or one of its fragments (dissolved in acidified saline containing 0.001 N HCl) was injected into the femoral vein or under the skin of the abdomen. Data were collected for 12 min after intravenous injection or for 22 min after subcutaneous injection. FIG. 8 shows the maximum drop in blood pressure and time to maximum drop on addition of 0.8 nmol/100 g dose of [Leu$^{27}$]cyclo(Glu$^{22}$-Lys$^{26}$)hPTH-(1–31)-NH$_2$ or [Leu$^{27}$]cyclo(Lys$^{26}$-Asp$^{30}$) hPTH-(1–31)-NH$_2$ for administration by either subcutaneous (open bar) or intravenous (hatched bar) route. The [Leu$^{27}$]cyclo(Glu$^{22}$-Lys$^{26}$)hPTH-(1–31)-NH$_2$ analogue shows increased bioavailability, as compared to [Leu$^{27}$] cyclo(Lys$^{26}$-Asp$^{30}$)hPTH-(1–31)-NH$_2$. This is indicated by the much shorter time needed to drop to the minimum bp after subcutaneous injection. Both cyclic analogues show enhanced hypotensive effects when injected subcutaneously, when compared to hPTH-(1–31)-NH$_2$. Thus, each cyclic lactam analogue, when injected subcutaneously, is expected to have more desirable properties than the linear counterpart, These include greater bioavailabilities, resulting from enhanced resistance to proteases and/or increased ability to be transported from lipidic environments. The latter could be due to the stabilization of the amphiphilic helix near the C-terminus of the hormone.

Further Results

For the purpose of these results, the peptides are identified as follows.

hPTH-(1–31)-NH$_2$ (1); [Leu$^{27}$]-hPTH-(1–31)-NH$_2$ (2) (FIG. 9); [Leu$^{27}$]cyclo(Glu$^{22}$-Lys$^{26}$)-hPTH-(1–31)-NH$_2$ (3) (FIG. 2); [Leu$^{27}$]cyclo(Lys$^{26}$-Asp$^{30}$)-hPTH-(1–31)-NH$_2$ (4); cyclo(Lys$^{27}$-Asp$^{30}$)-hPTH-(1–31)-NH$_2$ (5) (FIG. 10); hPTH-(1–30)-NH$_2$ (6); [Leu$^{27}$] hPTH-(1–30)-NH$_2$ (7); [Leu$^{27}$]cyclo(Glu$^{22}$-Lys$^{26}$)-hPTH-(1–30)-NH$_2$ (8)

Figure 12:
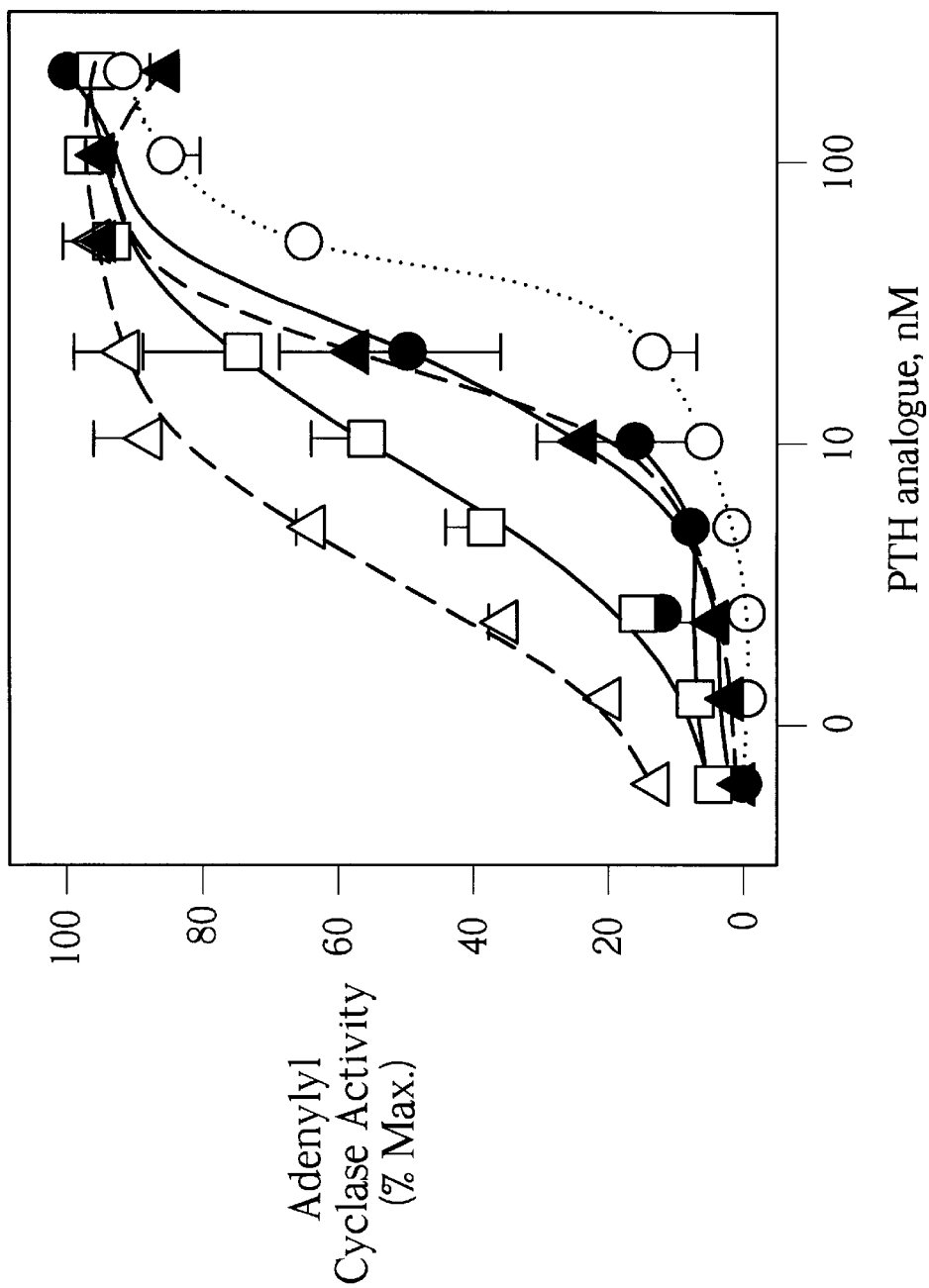
FIG. 12 shows the adenyl cyclase stimulating activities of various analogs according to the invention.

Adenylyl Cyclase Activities. We previously reported that [Leu$^{27}$]-hPTH-(1–34)-NH$_2$ is more active in stimulating AC activity in the ROS cell line than hPTH-(1–34)-NH$_2$.[5] We have also found that peptide 2 (EC$_{50}$, 11.5±5.2 nM) is more active than the native sequence 1, (EC$_{50}$, 19.9±3.9 nM) (FIG. 12). Shown are peptides 1(●); 2(□); 3(△) 4(▲) 5(○). Lactam formation between Glu$^{22}$ and Lys$^{26}$ (3) included a still greater AC-stimulating activity, with EC$_{50}$ values of 3.3±0.3 nM (FIG. 12). Thus, the net effect of this cyclization and replacement of Lys$^{27}$ with Leu is about a 6-fold increase in activity. In contrast, lactam formation between either Lys$^{26}$ and Asp$^{30}$ (4) or Lys$^{27}$ and Asp$^{30}$ (5) resulted in a lessening of adenylyl cyclase stimulation, with respect to their parent linear sequences. Thus, the 26–30 lactam (4) has slightly less activity than its linear form, with an EC$_{50}$ of 17.0±3.3 nM vs 11.5±5.2 nM for 2. The 27–30 lactam (5) more markedly reduces the activity of the parent linear peptide, having an EC$_{50}$ of 40.3±4.4 nM as compared to 19±3.9 nM for 1.

We have previously reported that hPTH-(1–30)-NH$_2$ (6) has an AC-stimulating activity (EC$_{50}$, 20 nM), close to that of analogue 1. We have now found that [Leu$^2$]-hPTH-(1–30)-NH$_2$ (7) and cyclo(Glu$^{22}$-Lys$^{26}$)-hPTH-(1–30)-NH$_2$ (8) (FIG. 11) have similar AC-stimulating activities to peptide 6.

Hypotensive Effects

Figure 13:
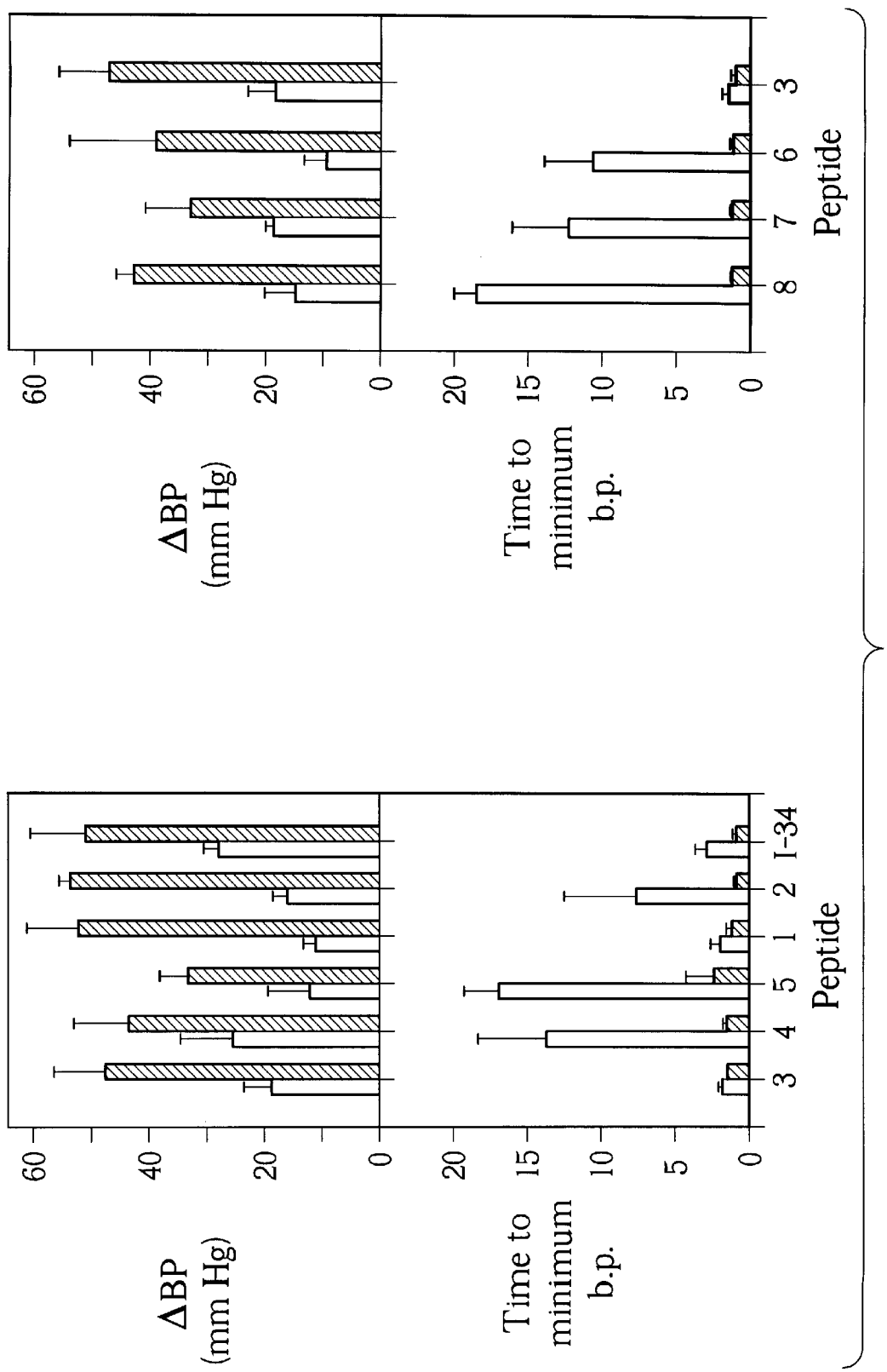
FIG. 13 shows hypotensive activity of the cyclic analogues $[Leu^{27}]cyclo(Glu^{22}$-$Lys^{26})$-hPTH-(1–31)-$NH_2$ and $[Leu^{27}]cyclo(Glu^{22}$-$Lys^{26})$hPTH-(1–30)-$NH_2$ as compared to linear analogues hPTH-(1–30)-$NH_2$ and $[Leu^{27}]$hPTH-(1–30)-$NH_2$.

FIG. 13 shows the hypotensive action of linear (6 and 7) and cyclic lactam analogues (3 and 8). Shown are the maximum drops in blood pressure (upper) obtained on injecting the rat with 0.8 nmol/100 g of body weight the analogue and the time taken to attain the maximum drop in blood pressure (lower). The analogues (left to right, peptides 8,7, 6, 3) were injected either intravenously (shaded bar) or subcutaneously (open bar). Removal of Val$^{31}$ resulted in all of analogues 6, 7, and 8 having significantly (p<0.05) reduced rates of transport of the subcutaneously injected peptides to the vascular system (FIG. 13). The actual total blood pressure drops of peptides 6 and 8 were, nonetheless, not significantly different (p>0.05) from those of the other analogues, whether subcutaneously or intravenously administered, with the exception of peptide 5.

Assay Correlating Hypotensive Effect With Osteogenic Activity

As described in Example 6 and illustrated in FIG. 8, a fast hypotensive effect observed following subcutaneous injection of hPTH analogs correlates with osteogenic activity. Accordingly, the assay is useful for screening candidate hPTH analogs for osteogenic effect and to eliminate non-hypotensive constructs, without having to sacrifice laboratory test animals.

By way of background, we have used a unique set of osteogenic and non-osteogenic AC-, AC/PLC-, or PLC-activating PTH fragments to definitively prove that it is only AC stimulation that reduces blood pressure and to compare the hypotensive actions of these fragments when they are injected subcutaneously or intravenously into female rats. We have shown that the hypotensive response is triggered only by AC- or AC/PLC-stimulating fragments and that it is the relatively small hypotensive response to subcutaneous injection, and not the much larger response to intravenous injection, that correlates with the osteogenic activities of hPTH-(1–31)NH$_2$, hPTH-(1–34), and hPTH-(1–84) in OVX-rats, but not to hPTH-(1–30)NH$_2$, which stimulates AC and reduces blood pressure, but does not stimulate bone formation.

Specifically, hPTH-(1–84), and its hPTH-(1–34), hPTH-(1–31)NH$_2$, and hPTH-(1–30)NH$_2$ fragments reduced the tail artery pressure in anesthetized female Sprague-Dawley rats by 42.4–67.1% within about 1 minute after injection into a femoral vein, but reduced the pressure by only 8.5–36.2% 2–19 minutes after subcutaneous injection. hPTH-(1–84) and hPTH-(1–34) stimulate both adenylyl cyclase and phospholipase-C in their target cells, but the hypotensive action must have been stimulated specifically by adenylyl cyclase activation, because hPTH-(1–30)NH$_2$ and hPTH-(1–31)NH$_2$ which can only stimulate adenyl cyclase, were potently hypotensive when injected intravenously whereas hPTH-(7–84), which can only stimulate phosholipase-C, was not significantly hypotensive when injected intravenously. Since PTH's osteogenic action is also mediated by adenylyl cyclase stimulation, it was expected that the hypotensive response might be used to screen new PTH constructs for possible osteogenicity. Indeed, the osteogenic activities of subcutaneously injected hPTH-(1–31)NH$_2$, hPTH-(1–34), and hPTH-(1–84) correlated closely to their hypotensive activities, with hPTH-(1–34) being much more hypotensive and significantly more osteogenic than the other two molecules. hPTH-(1–31)NH$_2$ and hPTH-(1–84) were equally osteogenic and hypotensive. However, this correlation broke down with hPTH-(1–30) NH$_2$ which stimulates AC almost as strongly as hPTH-(1–31)-NH and hPTH-(1–34) and reduces blood pressure as much as hPTH-(1–31)-NH$_2$ but does not stimulate bone formation. Nevertheless, the ability to significantly reduce arterial pressure is a common property of osteogenic PTH and PTH fragments and is thus a rapidly determinable preliminary indicator of in vivo bioactivity of PTH fragments.

More specifically, both hPTH-(1–34) and hPTH-(1–31)-NH$_2$ were maximally hypotensive at 0.8 nmol/100 g of body weight.

This hypotensive response was accompanied by a transient (20–30 minute) reddening of the rats' ears and paws, which can be considered as a useful visual qualitative marker.

Though AC- or AC/PLC-stimulating fragments were potently hypotensive when injected intravenously, an intravenous injection of 0.8 nmol/100 g of body weight of hPTH-(7–84), which can only stimulate PLC, very slowly (9.8±2.0 minute) and only very slightly, reduced the tail artery pressure by 3.28±1.0 mm Hg compared with the prompt (0.9±0.08 minutes) 43.2±5.8 mm Hg reduction caused by the AC/PLC-stimulating hPTH-(1–84) or the equally prompt 51.6±3.3 mm Hg fall caused by the AC stimulating hPTH-(1–31)$NH_2$.

One subcutaneous injection of an AC- or AC/PLC-stimulating fragment caused a much slower and smaller reduction in the tail artery pressure than an intravenous injection of the same dose. For example, 0.8 nmol/100 g of body weight of hPTH-(1–34) reduced the pressure by only 27.9±3.6 mm Hg when injected subcutaneously as compared with 50.9±5.6 mm Hg when injected intravenously. The same dose of hPTH-(1–31)$NH_2$ reduced the blood pressure by only 11.1±1.6 mm Hg when injected subcutaneously as compared with 51.6±3.3 mm Hg when injected intravenously.

There was no significant difference between the rapid and large reductions in the tail artery pressure caused by intravenously injected hPTH-(1–84), hPTH-(1–34), and hPTH-(1–31)$NH_2$, but hPTH-(1–34), was at least twice as effective ($P<0.01$) as the other two molecules when injected subcutaneously.

One of the factors that affects the hypotensive action and osteogenicity of subcutaneously injected PTH or a PTH fragment is its ability to move without being inactivated from the injection site to its targets first in the vasculature and then into the bones. This ability is reflected in the time required for the tail artery pressure to fall to its minimum value after injection. Shortening the PTH molecule C-terminally from 84 to 31 residues eliminated the ability to stimulate PLC without diminishing the ability to stimulate AC and it decreased by nine times the amount of time required for the tail artery pressure to reach its minimum. Removing one more residue to make hPTH-(1–30)$NH_2$ dramatically increased the amount of time required for the blood pressure to fall to its minimum from 2.0±0.31 minutes in the case of hPTH-(1–31)$NH_2$ to 13.8±2.3 minutes. However, it is important to note that hPTH-(1–31)$NH_2$ took no longer to reduce the blood pressure than hPTH-(1–84).

The use in the present study of hPTH-(1–31)$NH_2$, the first PTH construct to be able to stimulate AC as strongly as hPTH-(1–34) without activating PLC and stimulating membrane-associated PKCs activity, has now provided the most direct proof that PTH's hypotensive action is due entirely to AC activation. Thus, although intravenous injection of 0.8 nmol/100 g of body weight of hPTH-(7–84), which can only stimulate PLC/PKCs, did not significantly affect tail artery pressure, intravenous injection of the same dose of hPTH-(1–31)$NH_2$ dropped the pressure as much as hPTH-(1–34).

Since AC also mediates the PTH-induced stimulation of cortical and trabecular bone formation in OVX rats, the triggering of a hypotensive response in intact female rats appears to be a simple, rapidly measurable indicator of a PTH construct's possible osteogenicity. On the other hand, failure to reduce arterial pressure would eliminate a fragment from further assessment, thus avoiding unnecessary, expensive, long-term osteogenicity test in OVX rats. The hypotensive responses to intravenous injection of the PTHs were not correlated to osteogenicities. However, the much smaller hypotensive responses to subcutaneously-injected hPTH-(1–31)$NH_2$, hPTH-(1–34), and hPTH-(1–84) did parallel the osteogenicites of these molecules, with hPTH-(1–34) having the strongest hypotensive and osteogenic actions and the other two molecules being as effective as each other, but less effective than hPTH-(1–34), in reducing the blood pressure and stimulating bone formation. But this correlation broke down with hPTH-(1–30)$NH_2$ which stimulates AC almost as strongly as hPTH-(1–31)$NH_2$ and hPTH-(1–34) and reduced blood pressure as much as hPTH-(1–31)$NH_2$ but does not stimulate bone formation[1]. The reason for this lack of osteogenicity is unknown. It cannot be due only to subcutaneously injected hPTH-(1–30)$NH_2$ needing more time to reduce the blood pressure, because subcutaneously injected hPTH-(1–84) needs the same amount of time to reduce the blood pressure, yet is strongly osteogenic. Clearly the osteogenic response depends on many different factors that combine to enable the arrival from the injection site of enough active hormone or hormone fragment at target PTH receptor-expressing mature osteoblasts. The failure of the AC-stimulating, blood pressure-reducing hPTH-(1–30)$NH_2$ to stimulate bone formation might be the result of a combination of greater instability, a slightly higher $EC_{50}$ for AC stimulation i.e. 20 nM instead of the 16 nM for hPTH-(1–31)$NH_2$ (SEQ ID NO:1) and hPTH-(1–34) (SEQ ID NO:22) and a long time to enter the circulation from the injection site.

Despite the failure of hPTH-(1–30)$NH_2$ to be osteogenic, the ability to significantly reduce arterial pressure is still a common property of the osteogenic PTHs and is therefore a rapidly determinable indicator of possible in vivo bioactivity of PTH fragments. It follows that the hypotensive response should also serve as an effective indicator of the ability of an osteogenic PTH construct to reach its targets after administration by oral or other noninjectable routes.

The discomfort and other possible sequelae of a hypotensive reaction to each injection might limit the willingness of osteoporotic patients to accept long-term treatment with PTH or a PTH fragment. Fortunately, intermittent subcutaneous injections of the PTHs are currently used to stimulate bone formation and these molecules are all far less hypotensive when injected subcutaneously than when injected intravenously. As we have also argued previously[6,7], hPTH-(1–31)$NH_2$ would have the added advantage of stimulating AC without stimulating PLC and any potential $Ca^{2+}$- and PKCs-mediated side-effects it might trigger.

EXAMPLE 7

Cyclo($Lys^{27}$-$Asp^{30}$)-hPTH-(1–31)-$NH_2$ (5.) The synthesis was performed in an analogous manner to that of [$Leu^{27}$]-cyclo($Glu^{22}$-$Lys^{26}$)-hPTH-(1–31)-$NH_2$.

The product had an estimated purity of >95%, with a molecular mass of 3700.64 (±0.38) (expected M+1= 3700.14). The peptide was sequenced to confirm the lactam position.

[$Leu^{27}$]-cyclo($Glu^{22}$-$Lys^{26}$)-hPTH-(1–31)-$NH_2$ (8). This peptide was synthesized as for peptide 3, without manual addition of Val to the support. The product had an estimated purity of >97%, with a molecular mass of 3586.14 (±0.19) (expected M+1=3685.99).

The analogues of the present invention may be administered to a warm-blooded mammal, in need thereof, particularly a human, by parenteral, topical, or rectal administration, or by inhalation or by oral delivery. The analogues may be conventionally formulated in a parenteral dosage form compounding about 1 to about 300 mg per unit of dosage with a conventional vehicle, excipient, binder, preservative, stabilizer, color, agent or the like as called for by accepted pharmaceutical practice.

For parenteral administration, a 1 to 2 ml painless subcutaneous injection through an ultra-fine 30 gauge syringe needle would need to be given no more than once daily, for one to 2 years, depending on the severity of the disease. The injected material would contain one of the present invention in an aqueous, isotonic, sterile solution or suspension (optionally with a preservative such as phenol or a solubilizing agent such as ethylenediamine tetraacetic acid (EDTA)). Among the acceptable vehicles and solvents that may be employed are water, mildly acidified water, Ringer's solution and isotonic sodium chloride solution. In addition, sterile, fixed oils are conventionally employed as a solvent or suspending medium. Synthetic monoglycerides, diglycerides, fatty acids (such as oleic acid) find use as a fixed oil in the preparation of injectables.

For rectal administration, the analogues of the present invention can be prepared in the form of suppositories by mixing with a suitable non-irritating excipient such as cocoa butter or polyethylene glycols.

For topical use, the analogues of the present invention can be prepared in the form of ointments, jellies, solutions, suspensions of dermal adhesive patches.

For inhalation, this can be achieved, for example, by means described in PCT publication application no. WO94/07514, the disclosure of which is incorporated herein by reference.

The daily dose should not have to exceed 0.05 mg/kg of body weight, or about 3.5 mg/70 kg human, depending on the activity of the specific compound, the age, weight, sex, and conditions of the subject being treated. As would be well known, the amount of active ingredient that may be combined with the carried materials to produce a single dosage will vary depending upon the host treated and the particular mode of administration.

The following tabulated list of analogues were all produced in accordance with the procedures described above.

TABLE 1

Molecular Masses of PTH Analogues

| SEQ ID | Analogue | Mass (determined) | Mass (expected) (M + 1) |
|---|---|---|---|
| 1 | hPTH-(1–31)-NH$_2$ | 3717.77 (±0.13) | 3717.14 |
| 3 | [Leu$^{27}$]cyclo(Glu$^{22}$-Lys$^{26}$)-hPTH-(1–31)-NH$_2$ | 3685.46 (±0.46) | 3685.12 |
| 7 | [Leu$^{27}$]cyclo(Glu$^{22}$-Lys$^{26}$)-hPTH-(1–30)-NH$_2$ | 3586.14 (±0.19) | 3585.99 |
| 4 | [Leu$^{27}$]cyclo(Lys$^{26}$-Asp$^{30}$)-hPTH-(1–31)-NH$_2$ | 3685.61 (±0.36) | 3685.12 |
| 6 | cyclo(Lys$^{27}$-Asp$^{30}$)-hPTH-(1–31)NH$_2$ | 3700.54 (±0.38) | 3700.14 |
| 8 | [Leu$^{27}$]cyclo(Glu$^{22}$-Lys$^{26}$)-hPTH-(1–31)-OH | 3685.96 (±0.07) | 3686.12 |
| 9 | [Leu$^{27}$]cyclo(Glu$^{22}$-Lys$^{26}$)-hPTH-(1–34)-NH$_2$ | 4083.62 (±0.33) | 4083.52 |
| 10 | [Leu$^{27}$]cyclo(Glu$^{22}$-Lys$^{26}$)-hPTH-(1–34)-OH | 4084.14 (±0.87) | 4084.52 |
| 11 | [Ala$^{27}$]cyclo(Glu$^{22}$-Lys$^{26}$)-hPTH-(1–31)-NH$_2$ | 3642.70 (±0.76) | 3643.04 |
| 12 | [Nle$^{27}$]cyclo(Glu$^{22}$-Lys$^{26}$)-hPTH-(1–31)-NH$_2$ | 3684.57 (±0.99) | 3685.12 |
| 13 | [Nle$^{8,18}$;Leu$^{27}$]cyclo(Glu$^{22}$-Lys$^{26}$)-hPTH-(1–31)-NH$_2$ | 3649.50 (0.59) | 3649.04 |
| 14 | cyclo(Glu$^{22}$-Lys$^{26}$)-hPTH-(1–31)-NH$_2$ | 3699.66 (±0.49) | 3700.14 |
| 15 | [Ile$^{27}$]cyclo(Glu$^{22}$-Lys$^{26}$)-hPTH-(1–31)-NH$_2$ | 3684.76 (±0.74) | 3685.12 |
| 16 | [Tyr$^{27}$]cyclo(Glu$^{22}$-Lys$^{26}$)-hPTH-(1–31)-NH$_2$ | 3734.47 (±0.80) | 3735.14 |
| 17 | α-acetyl-[Leu$^{27}$]cyclo(Glu$^{22}$-Lys$^{26}$)-hPTH-(1–31)-NH$_2$ | 3726.25 (±0.42) | 3727.12 |
| 18 | [Leu$^{27}$]cyclo(Lys$^{22}$-Glu$^{26}$)-hPTH-(1–31)-NH$_2$ | 3684.67 (±0.52) | 3685.12 |
| 19 | [Leu$^{27}$]cyclo(Asp$^{22}$-Orn$^{26}$)-hPTH-(1–31)-NH$_2$ | 3656.90 (±0.67) | 3657.12 |
| 20 | [Cys$^{22}$;Cys$^{26}$;Leu$^{27}$]cyclo(Cys$^{22}$-Cys$^{26}$)hPTH(1–31)NH$_2$ | 3651.26 ± 0.31 | 3650.1 |
| 21 | [Cys$^{26}$;Cys$^{30}$;Leu$^{27}$]cyclo(Cys$^{26}$-Cys$^{30}$)hPTH(1–31)NH$_2$ | 3553.61 ± 0.16 | 3664.13 |

TABLE 2

Adenylyl Cyclase (AC) Activities of Peptide Analogues

| SEQ ID | Analogue | Adenylyl Cyclase (EC$_{50}$) |
|---|---|---|
| 1 | hPTH-(1–31)-NH$_2$ | 20 |
| 3 | [Leu$^{27}$]cyclo(Glu$^{22}$-Lys$^{26}$)-hPTH-(1–31)-NH$_2$ | 3 |
| 7 | [Leu$^{27}$]cyclo(Glu$^{22}$-Lys$^{26}$)-hPTH-(1–30)-NH$_2$ | 20 |
| 4 | [Leu$^{27}$]cyclo(Lys$^{26}$-Asp$^{30}$)-hPTH-(1–31)-NH$_2$ | 3*, 17** |
| 6 | cyclo(Lys$^{27}$-Asp$^{30}$)-hPTH-(1–31)-NH$_2$ | 40 |
| 8 | Leu$^{27}$]cyclo(Glu$^{22}$-Lys$^{26}$)-hPTH-(1–31)-OH | 7 |
| 9 | [Leu$^{27}$]cyclo(Glu$^{22}$-Lys$^{26}$)-hPTH-(1–34)-NH$_2$ | 8 |
| 10 | [Leu$^{27}$]cyclo(Glu$^{22}$-Lys$^{26}$)-hPTH-(1–34)-OH | 6 |
| 11 | [Ala$^{27}$]cyclo(Glu$^{22}$-Lys$^{26}$)-hPTH-(1–31)-NH$_2$ | 9 |
| 12 | [Nle$^{27}$]cyclo(Glu$^{22}$-Lys$^{26}$)-hPTH-(1–31)-NH$_2$ | 9 |
| 13 | [Nle$^{8,18}$;Leu$^{27}$]cyclo(Glu$^{22}$-Lys$^{26}$)-hPTH-(1–31)-NH$_2$ | 6 |
| 14 | cyclo(Glu$^{22}$-Lys$^{26}$)-hPTH-(1–31)-NH$_2$ | 17 |
| 15 | [Ile$^{27}$]cyclo(Glu$^{22}$-Lys$^{26}$)-hPTH-(1–31)-NH$_2$ | 9 |
| 16 | [Tyr$^{27}$]cyclo(Glu$^{22}$-Lys$^{26}$)-hPTH-(1–31)-NH$_2$ | 9 |
| 17 | α-acetyl-[Leu$^{27}$]cyclo(Glu$^{22}$-Lys$^{26}$)-hPTH-(1–31)-NH$_2$ | 24 |
| 18 | [Leu$^{27}$]cyclo(Lys$^{22}$-Glu$^{26}$)-hPTH-(1–31)-NH$_2$ | 4 |
| 19 | [Leu$^{27}$]cyclo(Asp$^{22}$-Orn$^{26}$)-hPTH-(1–31)-NH$_2$ | >200 |

TABLE 2-continued

Adenylyl Cyclase (AC) Activities of Peptide Analogues

| SEQ ID | Analogue | Adenylyl Cyclase (EC$_{50}$) |
|---|---|---|
| 20 | [Cys$^{22}$;Cys$^{26}$;Leu$^{27}$]cyclo(Cys$^{22}$-Cys$^{26}$)hPTH(1–31)NH$_2$ | 16 |
| 21 | [Cys$^{26}$;Cys$^{30}$;Leu$^{27}$]cyclo(Cys$^{26}$-Cys$^{30}$)hPTH(1–31)NH$_2$ | 24 |

*FIG. 4
**FIG. 12

REFERENCES

The disclosures of the following references are incorporate herein by reference.

(1) Caulfield, M. P.; McKee, R. L.; Goldman, M. E., Duong, L. T.; Fisher, J. E.; Gay, C. T.; DeHaven, P. A.; Levy, J. J.; Roubini, E.; Nutt, R. F.; Chorev, M.; Rosenblatt, M. The Bovine Renal Parathyroid Hormone(PTH) Receptor Has Equal Affinity for 2 Different Amino Acid Sequences—The Receptor Binding Domains of PTH and PTH-Related Protein Are Located Within the 14–34 Region. *Endocrinology* 1990, 127,83–87.

(2) Neugebauer, W.; Barbier, J.-R.; Sung, W. L.; Whitfield, J. F.; Willick, G. E. Solution Structure and Adenylyl Cyclase Stimulating Activities of C-Terminal Truncated Human Parathyroid Hormone Analogues *Biochemistry* 1995, 34, 8835–8842.

(3) Gardella, T. J.; Wilson, A. K.; Keutmann, H. T.; Oberstein, R.; Potts, J. T.; Kronenberg, H. M., and Nussbaum, S. R. Analysis of Parathyroid Hormone's Principal Receptor-Binding Region by Site-Directed Mutagenesis and Analog Design. Endocrinology 1993, 132, 2024–2030.

(4) Marqusee, S.; Baldwin, R. L. Helix Stabilization by Glu . . . Lys+ Salt Bridges in Short Peptides of De Novo Design. *Proc. Natl. Acad. Sci. U.S.A.* 1987. 84,8898–8902.

(5) Surewicz, W. K.; Neugebauer, W.; Gagnon, L.; MacLean, S.; Whitfield, J. F.; Willick, G. E. Structure-Function Relationships in Human Parathyroid Hormone: The Essential Role of Amphiphilic-Helix. In *Peptides: Chemistry, Structure, and Biology* 1993; Smith, J.; Hodges, R., Eds.; ESCOM Leiden, The Netherlands, 1993, pp. 556–558.

(6) Whitfield, J. F.; Morley, P.; Willick, G. E.; Ross, V.; Barbier, J. R.; Isaacs, R. J.; Ohannessianbarry, L. Stimulation of the Growth of Femoral Trabecular Bone in Ovariectomized Rats by the Novel Parathyroid Hormone Fragment, hPTH-(1–31)NH$_2$ (Ostabolin) *Calcif. Tissue Int.* 1996, 58, 81–87.

(7) Whitfield, J. F.; Morley, P. Small Bone-Building Fragments of Parathyroid Hormone: New Therapeutic Agents for Osteoporosis *Trends Pharmacol. Sci.* 1995 16, 382–386.

We claim:

1. A human parathyroid hormone hPTH analogue or pharmaceutically acceptable salts thereof, having the amino acid sequence:

H-NH-Ser-Val-Ser-Glu-Ile-Gln-Leu-Met-His-Asn-Leu-Gly-Lys-R3-R4-R5-R6-Met-Glu-Arg-Val-Glu-Trp-Leu-Arg-Lys-R11-Leu-Gln-Asp-NH$_2$ (SEQ ID NO:33)

wherein

R3=His or a water soluble amino acid,
R4=Leu or a water soluble amino acid,
R5=Asn or a water soluble amino acid,
R6=Ser or a water soluble amino acid,
R11=Lys or Leu, cyclized in the form of a lactam between amino acid pairs 22 and 26; 26 and 30; or 27 and 30 when R11 is Lys, provided the analogue is not SEQ ID NO:7.

2. An analogue according to claim 1, wherein the cyclisation is either between $Glu^{22}$ and $Lys^{26}$ or between $Lys^{26}$ and $Asp^{30}$.

3. An analogue according to claim 1, wherein R3 is His or Lys, R4 is Leu, Lys or Arg, R5 is Asn, Orn, Hci, Asp, Arg, Lys, D-Lys, Ser or Gly, and R6 is Ser, Lys, Asp or Arg.

4. An analogue according to claim 1, wherein R3–R6 is His-Lys-Lys-Lys, His-Leu-Lys-Lys, Lys-Lys-Lys-Lys or His-Leu-Lys-Ser (SEQ ID NOS: 28–31).

5. A composition for administration to a warm-blooded animal comprising a human parathyroid hormone analogue according to claim 1 in association with a pharmaceutically acceptable carrier or excipient.

6. A method of treating osteoporosis in a warm-blooded animal in need of such treatment, comprising administering to such warm-blooded animal, a therapeutically effective amount of a human parathyroid hormone analogue according to claim 1.

7. A method according to claim 6 wherein the human parathyroid analogue is cyclized as a lactam between amino acid pairs 22 and 26.

8. A human parathyroid hormone hPTH analogue or pharmaceutically acceptable salts thereof, having the amino acid sequence:

H-NH-Ser-Val-Ser-Glu-Ile-Gln-Leu-Met-His-Asn-Leu-Gly-Lys-R3-R4-R5-R6-Met-Glu-Arg-Val-Glu-Trp-Leu-Arg-Lys-R11-Leu-Gln-Asp-OH (SEQ ID NO:33)

wherein

R3=His or a water soluble amino acid,
R4=Leu or a water soluble amino acid,
R5=Asn or a water soluble amino acid,
R6=Ser or a water soluble amino acid,
R11=Lys or Leu, cyclized in the form of a lactam between amino acid pairs 22 and 26; 26 and 30; or 27 and 30 when R11 is Lys.

9. A human parathyroid hormone hPTH analogue or pharmaceutically acceptable salts thereof, having the amino acid sequence:

H-NH-Ser-Val-Ser-Glu-Ile-Gln-Leu-Met-His-Asn-Leu-Gly-Lys-R3-R4-R5-R6-Met-Glu-Arg-Val-R8-Trp-Leu-Arg-R10-R11-Leu-Gln-R13-NH$_2$ (SEQ ID NO:33)

wherein

R3=His or a water soluble amino acid,
R4=Leu or a water soluble amino acid,
R5=Asn or a water soluble amino acid,
R6=Ser or a water soluble amino acid,
R8=Cys or Glu
R10=Cys,
R11=Lys or Leu,
R13=Asp or Cys cyclized in the form of a disulfide bridge between Cys pairs 22/26 or 26/30.

10. A human parathyroid hormone hPTH analogue or pharmaceutically acceptable salts thereof, having the amino acid sequence:

H-NH-Ser-Val-Ser-Glu-Ile-Gln-Leu-Met-His-Asn-Leu-Gly-Lys-R3-R4-R5-R6-Met-Glu-Arg-Val-R8-Trp-Leu-Arg-R10-R11-Leu-Gln-R13-OH (SEQ ID NO:34)

wherein

R3=His or a water soluble amino acid,
R4=Leu or a water soluble amino acid,
R5=Asn or a water soluble amino acid,
R6=Ser or a water soluble amino acid,
R8=Glu or Cys
R10=Cys
R11=Lys or Leu
R13=Asp or Cys cyclized in the form of a disulfide bridge between Cys pairs 22/26 or 26/30.

11. A human parathyroid hormone hPTH analogue or pharmaceutically acceptable salts thereof, having the amino acid sequence:

H-NH-Ser-Val-Ser-Glu-Ile-Gln-Leu-Met-His-Asn-Leu-Gly-Lys-R3-R4-R5-R6-Met-Glu-Arg-Val-R8-Trp-Leu-R9-R10-R11-Leu-R12-R13-NH$_2$ (SEQ ID NO:35)

wherein

R3=His or a water soluble amino acid,
R4=Leu or a water soluble amino acid,
R5=Asn or a water soluble amino acid,
R6=Ser or a water soluble amino acid,
R8=Lys, Asp, Cys, Orn or Glu,
R9=Arg, Cys, Lys, Orn, His or Glu
R10=Glu, Orn, Cys, Asp or Lys,
R11=Lys, Gln, Ile, Nle, Leu, Tyr, Ala or Asp,
R12=Gln, Glu, Asp, Lys or Orn and
R13=Asp, Glu, Orn or Lys cyclized in the form of a lactam between amino acid pairs 22 and 26; 26 and 30; or 27 and 30 when R11 and R13 are Lys or Asp; or 25 and 29 when R9 and R12 are Lys, Orn, Glu or Asp, or cyclized in the form of a disulfide bridge between Cys pairs 22/26 or 26/30, provided the analogue is not SEQ ID NO:7.

12. A human parathyroid hormone hPTH analogue or the pharmaceutically acceptable salts thereof, having the amino acid sequence of SEQ ID NO:7.

13. A method of treating osteoporosis in a warm-blooded animal in need of such treatment comprising administering to such warm-blooded animal, a therapeutically effective amount of a human parathyroid hormone analogue of SEQ ID NO:7.

* * * * *

UNITED STATES PATENT AND TRADEMARK OFFICE
CERTIFICATE OF CORRECTION

PATENT NO.    : 6,110,892
DATED         : August 29, 2000
INVENTOR(S)   : Barbier et al.

Page 1 of 1

It is certified that error appears in the above-identified patent and that said Letters Patent is hereby corrected as shown below:

<u>Title page,</u>
Item [73], Inventors, delete inventors "Witold Neugebauer and Virginia J. S. Ross"

Signed and Sealed this

Twentieth Day of August, 2002

*Attest:*

JAMES E. ROGAN
*Attesting Officer*     *Director of the United States Patent and Trademark Office*